United States Patent [19]
Tripp et al.

[11] Patent Number: 6,100,390
[45] Date of Patent: Aug. 8, 2000

[54] PARASITIC HELMINTH P22U NUCLEIC ACID MOLECULES

[75] Inventors: Cynthia Ann Tripp; Glenn Robert Frank; Robert B. Grieve, all of Ft. Collins, Colo.

[73] Assignees: Heska Corporation; Colorado State University Research Foundation, both of Ft. Collins, Colo.

[21] Appl. No.: 08/458,860

[22] Filed: Jun. 2, 1995

Related U.S. Application Data

[63] Continuation of application No. 08/109,391, Aug. 19, 1993, Pat. No. 5,639,876, which is a continuation of application No. 08/003,257, Jan. 12, 1993, abandoned, application No. 08/003,389, Jan. 12, 1993, and application No. 07/654,226, Feb. 12, 1991, said application No. 08/003,257, and application No. 08/003,389, each is a continuation-in-part of application No.07/654,226.

[51] Int. Cl.$^7$ .......................... C07H 21/04; C07H 21/02; C12P 21/06; C12P 71/04
[52] U.S. Cl. ..................... 536/23.7; 435/69.1; 435/69.3; 435/71.1; 536/22.1; 536/23.1; 536/24.32
[58] Field of Search ............................... 536/22.1, 24.32, 536/23.1, 23.7; 435/69.1, 69.3, 71.1

[56] References Cited

U.S. PATENT DOCUMENTS 4,842,999  6/1989  Fuller et al. ................................ 435/7

FOREIGN PATENT DOCUMENTS 0057599  3/1988  Japan .

OTHER PUBLICATIONS

Grieve et al Pharmaceutical Biotechnology 6 737–68, 1995, Abstract, 1995.
Suggs et al PNAS 78:6613–6617, 1981.
Dinman et al Experimental Parasitology 71:176–188, 1990.
Yang et al Biochemical & Biophysical Research 212: 1029–1039 (Abstract only), 1995.
Freedman et al The 39th Annual Meeting of the American Society of Tropical Med & Hygien p. 83, Abstract 21, 1990.
Frank Dissertation pp. 100–134 1992.
Rothel et al Immunology & Cell Biology 75:41–46, 1997 (Abstract only.
Parab, et al., "Characterization of a Monoclonal Antibody Against Infective Larvae of *Brugia Malayi*", pp. 169–174, 1988, *J. Immunol.*, vol. 64.
Petralanda, et al., "Studies on a Filarial Antigen With Collagenase Activity", pp. 51–59, 1986, *Mol. Biochem. Parasitol.*, vol. 19.
Philipp, et al., "Biochemical and Immunologic Characterization of a Major Surface Antigen of *Dirofilaria Immitis* Infective Larvae", pp. 2621–2627, 1986, *J. Immunol.*, vol. 136(7), Apr.
Richer, et al., "*Dirofilaria Immitis*: Proteases Produced By Third— And Fourth–Stage Larvae", pp. 213–222, 1992, *Exp. Parasitol.*, vol. 75.

Robertson, et al., "*Toxocara Canis*: Proteolytic Enzymes Secreted by the Infective Larvae in Vitro", pp. 30–36, 1989, *Exp. Parasitol.*, vol. 69.
Rogers, "Enzymes in the Exsheathing Fluid of Nematodes and Their Biological Significance," pp. 495–502, 1982, *J. Parasitol.*, vol. 12(6).
Scott, et al., "Surface–Associated Antigens of Second, Third and Fourth Stage Larvae of *Dirofilaria Immitis*", pp. 339–353, 1990, *Acta Tropica*, vol. 47.
Sher, et al., "Passive Transfer of Acquired Resistance to *Schistosoma Mansoni* in Laboratory Mice", pp. 347–357, 1975, *J. Parasitol.*, vol. 70.
Sim, et al., "Immune Responses in Human *Brugia Malayi* Infections: Serum Dependent Cell–Mediated Destruction of Infective Larvae in Vitro", pp. 362–370, 1982, *Trans. Roy. Soc. Trop. Med. Hyg.*, vol. 76(3).
Strosberg, et al., "Receptor–Based Assays", pp. 30–36, 1991, *Current Opin. in Biotech.*, vol. 2.
Tamashiro, et al., "Proteolytic Cleavage Of lgG and Other Protein Substrates By *Dirofilaria Immitis* Microfilarial Enzymes", pp. 149–154, 1987, *J. Parasitol.*, vol. 73.
Tanner, et al., "Dipetalonema Viteae (Filarioidea): Development of the Infective Larvae in Micropore Chambers Implanted Into Normal, Infected and Immunized Jirds", pp. 173–174, 1981, *Trans. Roy. Soc. Trop. Med. Hyg.*, vol. 75(1).
Wang, et al., "Parenteral Formulations of Proteins and Peptides: Stability and Stabilizers", pp. S3–S26, 1988, *J. Parent. Sci. Tech.*, vol. 42.
Willadsen, et al., "Immunologic Control of a Parasitic Arthropod, Identification of a Protective Antigen from *Boophilus Microplus*", pp. 1346–1351, 1989, *J. Immunol.*, vol. 143, Aug.
Young, et al., "Efficient Isolation of Genes by Using Antibody Probes", pp. 1194–1198. 1983, *Proc. Natl. Acad. Sci. USA*, vol. 80, Mar.

(List continued on next page.)

*Primary Examiner*—James C. Housel
*Assistant Examiner*—Rodney P. Swartz
*Attorney, Agent, or Firm*—Sheridan Ross P.C.

[57] ABSTRACT

The present invention relates to isolated parasitic helminth nucleic acid sequences capable of hybridizing, under stringent conditions, to at least a portion of *D. immitis* nucleic acid sequence p4 and/or to at least a portion of *D. immitis* nucleic acid sequence p22U; to isolated parasitic helminth proteins that are encoded by such parasitic helminth nucleic acid sequences and that are capable of selectively binding to at least one component of immune serum capable of inhibiting helminth development; and to antibodies raised against such isolated parasitic helminth proteins. The present invention also relates to therapeutic compositions comprising such isolated nucleic acid sequences, proteins and/or antibodies. The present invention also includes methods to produce and use such nucleic acids, proteins, antibodies and therapeutic compositions capable of protecting animals from parasitic helminth infection and, particularly, from heartworm infection.

11 Claims, 2 Drawing Sheets

OTHER PUBLICATIONS

Grieve, et al., "Induction of Protective Immunity in Dogs to Infection with *Dirofilaria Immitis* Using Chemically–Abbreviated Infections", pp. 373–379, 1988, *Am. J. Trop. Med. Hyg.*, vol. 39(4).

Grieve, et al., "Epidemiology of Canine Heartworm Infection", pp. 200–246, 1983, *Epidem. Rev.*, vol. 5.

Hewick, et al., "A Gas–Liquid Solid Phase Peptide and Protein Sequenator", pp. 7990–7997, 1981, *J. Biol. Chem.*, vol. 256(15).

Hotez, et al., "Isolation and Characterization of a Proteolytic Enzyme from the Adult Hookworm Ancylostoma Caninum", pp. 7343–7348, 1985, *J. Biol. Chem.*, vol. 260(12).

Ibrahim, et al., "Antigen Shedding from the Surface of the Infective Stage Larvae of *Dirofilaria Immitis*", pp. 89–97, 1989, *J. Parasitol.*, vol. 99.

Jwo, et al., "Fractionated Sera from *Schistosoma Mansoni* Infected Patients Confers Passive Protection in Mice", pp. 553–562, 1989, *Am. J. Trop. Med. Hyg.*, vol. 41(5).

Kassis, et al., "Antibody–Dependent Complement–Mediated Killing of Schistosomula in Intraperitoneal Diffusion Chambers in Mice", pp. 1659–1662, 1979, *J. Immunol.*, vol. 123(4), Oct.

Lackey, et al., "Extracellular Proteases Of Onchocerca", pp. 176–185, 1989, *Exp. Parasitol.*, vol. 68.

Lal, et al, "Characterization of Stage–Specific Antigens of Infective of the Filarial Parasite *Brugia Malayi*", pp. 2032–2038, 1988, *J. Immunol.*, vol. 140.

Maki, et al., "Demonstration of Carboxyl and Thiol Protease Activities in Adult *Schistosoma Mansoni, Dirofilaria Immitis, Angiostrongylus Cantohensis* and *Ascaris Suum*", pp. 31–37, 1986, *J. Helminthol.*, vol. 60.

McKerrow, et al., "Proteinases From Invasive Larvae Of The Trematode Parasite *Schistosoma Mansoni* Degrade Connective–Tissue And Basement–Membrane Macromolecules", pp. 47–51, 1985, *Biochem J.*, vol. 231.

McKerrow, et al., "*Schistosoma Mansoni*: Cercarial Degradation of a Radioactively Labeled Collagen Gel", pp. 249–254, 1982, *Exp. Parasitol.*, vol. 53.

McReynolds, et al., "A Large Cuticular Protein from *D. Immitis* that is Also an Excretory or Secretory Product," pp. 173–174, 1989, 38th Annual Meeting, *Am. J. Trop. Med. Hyg.*, Abstract #233, Dec.

McReynolds, et al., "Cloning of a Highly Repeated Protein Located in the Gut of Filarial Parasites," p. 295, 1989, 38th Annual Meeting, *Am. J. Trop. Med. Hyg.*, Abstract #445, Dec.

Mok, et al., "Solubilization of Epicuticular Antigen from *Dirofilaria Immitis* Third–Stage Larvae", pp. 173–182, 1988, *Mol. Biochem. Parasitol.*, vol. 31.

Noble, et al., "*Phylum Nematoda*", pp. 256–322, 1982 (See p. 256), *Parasitol: The Biology of Animal Parasites*, Section V.

Abraham, et al., "Passive Transfer of Protective Immunity to Larval *Dirofilaria Immitis* from Dogs to Balb/C Mice", pp. 254–257, 1991, *J. Parasitol.*, vol. 77(2).

Abraham, et al., "Genetic Control of Murine Immune Responses to Larval *Dirofilaria Immitis*", pp. 523–528, 1990, *J. Parasitol.*, vol. 76(4).

Abraham, et al., "*Dirofilaria Immitis*: Molting Process of Third–Stage Larvae", pp. 314–322, 1990, *Exp. Parasitol.*, vol. 70.

Abraham, et al., "Active and Passive Immunization of Mice Against Larval *Dirofilaria Immitis*", pp. 275–282, 1988, *J. Parasitol.*, vol. 74(2).

Amiri, et al., "The *Schistosomatium Douthitti Cerarial Elastase* is Biochemically and Structurally Distinct from that of *Schistosoma Mansoni*," pp. 113–120, 1988, *Mol. Biochem. Parasitol.*, vol. 28.

Awobuluyi, et al., "Immunureactivity of Cloned *Dirofilaria Immitis* Proteins in Dogs Following Vaccination with Irradiated Infective Larvae," p. 139, 1989, 38th Annual Meeting, *Am. J. Trop. Med. Hyg.*, Abstract #150, Dec.

Bianco, et al., "Developmentally Regulated Expression and Secretion of a Polymorphic Antigen by Onchocerca Infective–Stage Larvae", pp. 203–212, 1990, *Mol. Biochem. Parasitol.*, vol. 39.

Blair, et al., "Immunization of Dogs Against *Dirofilaria Immitis* by Means of Chemically Abbreviated Infections", 1982, *Fifth International Congress of Parasitol.*, Toronto, Canada, Aug.

Boyer, et al., "Differential Antigen Content and Isotype Recognition of *O. Volvulvus* Antigens from Nodules Removed from Guatemalan Children", p. 169, 1990, 39th Annual meeting, *Am. J. Trop. Med. Hyg.*, Abstract #221, Nov.

Chomczynski, et al., "Single–Step Method of RNA Isolation by Acid Guanidinium Thiocyanate–Phenol–Chloroform Extraction", pp. 156–159, 1987, *Anal. Biochem.*, vol. 162.

Coleman, et al., "Use of Implantable Intraperitoneal Diffusion Chambers to Study *Bordetella Pertussis* Pathogenesis: Growth and Toxin Production in Vivo", pp. 33–39, 1986, *J. Infect. Dis.*, vol. 154(1), Jul.

Culpepper, et al., "Molecular Characterization of a *Dirofilaria Immitis* cDNA Encoding a Highly Immunoreactive Antigen", pp. 51–62, 1992, *Mol. Biochem. Parasitol.*, vol. 54.

Dalton, et al., "Thiol Proteases Released in Vitro by *Fasciola Hepatica*", pp. 161–166, 1989, *Mol. Biochem. Parasitol.*, vol. 35.

Davis, et al., "Purification and Biochemical and Immunologic Characterization of a 25KD Glycoprotein from the Surface of *Dirofilaria Immitis* Fourth Stage Larvae", p. 256, 1988, 37th Annual Meeting, *Am. Soc. Trop. Med. Hyg.*, Abstract #404.

Delves, et al., "Neurosecretory–Like Material in 3rd– and 4th–Stage *Dirofilaria Immitis* Larvae (Nematoda: Filarioidea)", pp. 99–104, 1989, *J. Parasitol.*, vol. 99.

Denham, "Vaccination Against Filarial Worms Using Radiation–Attenuated Vaccines", pp. 105–111, 1980, *Inter. J. Nucl. Med. Biol.*, vol. 7.

Frank, et al., "Metabolic Labeling of *Dirofilaria Immitis* Third– and Fourth–Stage Larvae and Their Excretory–Secretory Products", pp. 950–956, 1991, *J. Parasitol.*, vol. 77(6).

Gamble, et al., "Purification of a 44 Kilodalton Protease which Mediates the Ecdysis of Infective *Haemonchus Contortus* Larvae", pp. 49–58 (1989), *Mol. Biochem. Parasitol.*, vol. 33.

Grieve, et al., "Identification of *Dirofilaria Immitis* Larval Anitgens with Immunoprophylactic Potential Using Sera from Immune Dogs", pp. 2511–2515, 1992, *J. Immunol.*, vol. 148(8), Apr.

Grieve, "Potential for Immunoprophylaxis Against Heartworm (*Dirofilaria Immitis*) Infection", pp. 187–190, 1989, *Proc. Heartworm Symp.*

PARASITIC HELMINTH P22U NUCLEIC ACID MOLECULES

CROSS-REFERENCE TO RELATED APPLICATIONS

The present application is a continuation application of U.S. application Ser. No. 08/109,391, filed Aug. 19, 1993, now U.S. Pat. No. 5,639,876 entitled "NOVEL PARASITIC HELMINTH PROTEINS", which is a continuation-in-part of U.S. patent application Ser. No. 08/003,257, filed Jan. 12, 1993, now abandoned, entitled "Reagents and Methods for Identification of Vaccines"; of U.S. patent application Ser. No. 08/003,389, filed Jan. 12, 1993, entitled "Immunogenic Larval Proteins"; and of U.S. patent application Ser. No. 07/654,226, filed Feb. 12, 1991, entitled "Reagents and Methods for Identification of Vaccines". Ser. Nos. 08/003,257 and 08/003,389 are also continuation-in-part of Ser. No. 07/654,222. Each of these applications is incorporated by reference herein in their entireties.

FIELD OF THE INVENTION

The present invention relates to novel parasitic helminth proteins, nucleic acid sequences encoding such proteins and antibodies raised against such proteins. The present invention also includes a method to obtain such nucleic acid sequences and proteins, and a method of using such nucleic acid sequences, antibodies, and proteins to protect animals from infection. The present invention particularly relates to specific *Dirofilaria immitis* nucleic acid sequences and proteins as well as their use to protect animals from heartworm infection.

BACKGROUND OF THE INVENTION

Parasitic helminth infections in animals, including humans, are typically treated by chemical drugs, because there are essentially no efficacious vaccines available. One disadvantage with chemical drugs is that they must be administered often. For example, dogs susceptible to heartworm are typically treated monthly to maintain protective drug levels. Repeated administration of drugs to treat parasitic helminth infections, however, often leads to the development of resistant strains that no longer respond to treatment. Furthermore, many of the chemical drugs are harmful to the animals being treated, and as larger doses become required due to the build up of resistance, the side effects become even greater.

It is particularly difficult to develop vaccines against parasitic helminth infections both because of the complexity of the parasite's life cycle and because, while administration of parasites or parasite antigens can lead to the production of a significant antibody response, the immune response is typically not sufficient to protect the animal against infection.

As for most parasites, the life cycle of *Dirofilaria immitis*, the helminth that causes heartworm, includes a variety of life forms, each of which presents different targets, and challenges, for immunization. Adult forms of the parasite are quite large and preferentially inhabit the heart and pulmonary arteries of an animal. Males worms are typically about 12 cm (centimeters) to about 20 cm long and about 0.7 mm to about 0.9 mm wide; female worms are about 25 cm to about 31 cm long and about 1.0 to about 1.3 mm wide. Sexually mature adults, after mating, produce microfilariae which are only about 300 µm (micrometers) long and about 7 µm wide. The microfilariae traverse capillary beds and circulate in the vascular system of the dog in concentrations of about $10^3$ to about $10^5$ microfilariae per ml of blood. One method of demonstrating infection in the dog is to detect the circulating microfilariae.

If the dog is maintained in an insect-free environment, the life cycle of the parasite cannot progress. However, when microfilariae are ingested by the female mosquito during blood feeding on an infected dog, subsequent development of the microfilariae into larvae occurs in the mosquito. The microfilariae go through two larval stages (L1 and L2) and finally become mature third stage larvae (L3) of about 1.1 mm length, which can then be transmitted back to the dog through the bite of the mosquito. It is this L3 stage, therefore, that accounts for the initial infection. As early as three days after infection, the L3 molt to the fourth larval (L4) stage, and subsequently to the fifth stage, or immature adults. The immature adults migrate to the heart and pulmonary arteries, where they mature and reproduce, thus producing the microfilariae in the blood. "Occult" infection with heartworm in dogs is defined as that wherein no microfilariae can be detected, but the existence of the adult heartworms can be determined through thoracic examination.

Heartworm not only is a major problem in dogs, which typically cannot even develop immunity upon infection (i.e., dogs can become reinfected even after being cured by chemotherapy), but is also becoming increasingly widespread in other companion animals, such as cats and ferrets. Heartworm infections have also been reported in humans. Other parasitic helminthic infections are also widespread, and all require better treatment, including a preventative vaccine program.

Although many investigators have tried to develop vaccines based on specific antigens, it is well understood that the ability of an antigen to stimulate antibody production does not necessarily correlate with the ability of the antigen to stimulate an immune response capable of protecting an animal from infection, particularly in the case of parasitic helminths. A large number of materials are immunogenic and produce sera which test positive in immunoassays for ability to react with the immunizing antigen, but which fail to protect the hosts against infection. Antibodies which neutralize the infective agent in in vitro assays are much more likely to protect against challenge in vivo. Accordingly, the use of serum simply resulting from immunization or from infection by a parasitic helminth to screen for candidate vaccines does not provide sufficient specificity to identify protective immunogens. On the other hand, serum or other components of blood from immunized animals which is demonstrably protective against infection would contain antibodies, cells, or other factors that could selectively bind to potential antigens that, if used as therapeutic compositions, would elicit immune responses that protect against challenge.

In most infectious diseases, particularly those such as parasitic infections that have long and complex development courses, it is difficult to verify the protective effect of serum or T-cells from exposed animals for use as a screening reagent. First, verification of protection against challenge is tedious, since the host animal would first have to be challenged with the infectious agent and shown to be protected before it could be shown that antibody components of serum, for example, could be used as a screen. The definition of protection under such a regimen is often complex. Second, even if a protective effect against challenge is shown, it is not clear to what components of the immune system the protection is due. The protective effect could be due to antibodies, cells, mediators of the immune system or to combinations thereof. Thus, although this method of obtaining the screening reagent is sometimes used, it is time-consuming and does not permit identification of protective components.

A method to determine the effectiveness of in vivo immunization protocols includes implanting diffusion chambers containing infectious agents into immunized animals and determining the effects of such immunizations on the implanted infectious agents. Grieve, et al., 1988, Am. J. Trop. Med. Hyg. 39, p. 373–379, for example, report that dogs which had been immunized against Dirofilaria immitis infection were supplied diffusion chambers containing infective larvae. The larvae in the chambers could then be evaluated for the effect of the previous immunizations. Abraham, et al., 1988 J. Parasit. 74, p. 275–282, report that mice which had been immunized with L3 were supplied diffusion chambers containing D. immitis third-stage larvae, and the effects on these larvae were used to determine the possible immunity of the mice putatively developed by such immunization. Thus, the papers disclose that implantation of diffusion chambers containing the infectious agent into an immunized animal provides a convenient assessment of the effectiveness of certain directly administered active immunization protocols, but do not describe the use of such chambers to monitor passively transferred protective effects of selected fractions of a target host bloodstream.

Protection against parasitic helminth infections is difficult to achieve because, as heretofore stated, the complexity of the parasitic infection makes the choice of a candidate immunogen for vaccination very difficult. Even naturally conferred immunity cannot be assured to exist, as dogs with previous or existing infections with D. immitis can be reinfected (see, for example, Grieve et al., 1983, Epidemiologic Reviews 5, p. 220–246). However, this review also reports that there is some evidence of a naturally occurring protective immune response, which apparently limits the population of mature worms in infected dogs.

Furthermore, it has been possible to induce protective immunity artificially. Wong, et al., 1974, Exp. Parasitol. 35, p. 465–474, reported the immunization of dogs with radiation-attenuated infective larvae. The dogs were protected to varying degrees upon challenge. Blair, et al., 1982 in Fifth International Congress of Parasitology, Toronto, Canada, reported successful immunization by infecting the dogs and terminating the infection at the fourth larval stage by chemotherapy.

Grieve, 1989, Proc. Heartworm Symp., p. 187–190, reviewed the status of attempts to produce vaccines against heartworm in dogs. This report summarizes the use of infective larvae implanted in an inert diffusion chamber which permits the influx of cells and/or serum from the host and outflow of parasite material from the chamber to assess the effectiveness of inoculation protocols in both dogs and mice. The use of immunization with infective larvae was demonstrated to be partially effective in protection against subsequent challenge.

An alternative approach to finding, for example, a heartworm vaccine has been to attempt to identify prominent antigens in the infective stage of D. immitis. Philipp, et al., 1986, J. Immunol. 136, p. 2621–2627, reports a 35-kilodalton (kD) major surface antigen of D. immitis third stage larvae which was capable of immunoprecipitation with sera from dogs carrying an occult experimental D. immitis infection or with sera from dogs immunized by irradiated third stage larvae. In addition, this group reported (Davis, et al., 1988, Abstract 404, 37th Annual Meeting, Am. Soc. Trop. Med. Hyg.) three major surface proteins of the L4 having molecular weights of 150 kD, 52 kD, and 25 kD. The 25 kD molecule seemed unique to L4 larvae.

Ibrahim, et al., 1989, Parasitol. 99, p. 89–97, using D. immitis L3 larvae labeled with $^{125}$I, showed that a 35 kD and 6 kD component were shed into the culture medium by developing parasites. They further showed that antibodies from immunized rabbits and infected dogs immunoprecipitated the 35 kD, but not the 6 kD, component.

Scott, et al, 1990, Acta Tropica 47, p. 339–353, reported characterization of the surface-associated molecules of D. immitis L2, L3, and L4 by radiolabeling techniques and SDS-PAGE. They found major labeled components of 35 kD and 6 kD in extracts from iodine-labeled L2 and L3; lactoperoxidase-catalyzed labeling revealed components of apparent molecular weights 66 kD, 48 kD, 25 kD, 16.5 kD, and 12 kD. Iodine labeling of surface-associated molecules of L4 gave molecules of apparent molecular weights of 57 kD, 40 kD, 25 kD, 12 kD, and 10 kD; lactoperoxidase-catalyzed labeling showed additional bands of 45 kD, 43 kD, and 3 kD. However, these antigens were identified using uncharacterized serum sources.

Other approaches to obtaining vaccines against parasites in general have focused on the production of neutralizing antibodies. For example, both in vitro studies by Tanner, et al., 1981, Trans. Roy. Soc. Trop. Med. Hyg. 75, p. 173–174 and by Sim et al., 1982, Trans. Roy. Soc. Trop. Med. Hyg. 76, p. 362–370, and in vivo studies by Parab et al., 1988, Immunol. 64, p. 169–174, have demonstrated that antibodies are effective alone or with other immune components in killing filarial L3 from Dipetalonema (Acanthocheilonema) viteae or Brugia malayi. Furthermore, passive immunity to Schistosoma mansoni has been transferred from immune rats or humans to normal mice (see, for example, Sher, et al., 1975, Parasitol. 70, p. 347–357; Jwo et al., 1989, Am. J. Trop. Med. Hyg. 41, p. 553–562). None of these studies involved the use of an in vivo assay to determine the ability of serum, or cellular, components to be a useful screening tool for identifying protective antigens. Neither has any of these studies yet identified an effective vaccine.

SUMMARY OF THE INVENTION

The present invention includes an isolated parasitic helminth nucleic acid sequence capable of hybridizing, under stringent conditions, to at least a portion of D. immitis nucleic acid sequence p4 and/or to at least a portion of D. immitis nucleic acid sequence p22U. A preferred isolated nucleic acid sequence encodes a protein capable of selectively binding to at least one component of immune serum that is capable of inhibiting helminth development. Another preferred nucleic acid sequence includes an oligonucleotide capable of hybridizing to at least one of the D. immitis nucleic acid sequences under stringent hybridization conditions. The present invention also includes recombinant molecules and recombinant cells that include isolated nucleic acids of the present invention. Also included is a method to produce isolated nucleic acid sequences of the present invention.

Another embodiment of the present invention includes an isolated parasitic helminth protein, or mimetope thereof, capable of selectively binding to at least one component of immune serum that is capable of inhibiting helminth development, the protein being encoded by a parasitic helminth nucleic acid sequence capable of hybridizing, under stringent conditions, to at least a portion of D. immitis nucleic acid sequence p4 and/or to at least a portion of *D. immitis* nucleic acid sequence p22U. Preferred immune serum is derived from an animal that is immune to infection by the helminth, and preferably from an animal immunized with third stage and/or fourth stage larvae. Also included is a method to produce such isolated proteins and mimetopes of the present invention.

Yet another embodiment of the present invention is an antibody capable of selectively binding to a parasitic helminth protein or mimetope thereof, the antibody being produced by a method that includes administering to an animal an effective amount of an isolated protein or mimetope of the present invention. Also included is a method to produce such antibodies.

Yet another embodiment of the present invention is a therapeutic composition capable of protecting an animal from parasitic helminth infection when administered to the animal in an effective manner. The therapeutic composition includes at least one of the following therapeutic compounds: an isolated nucleic acid sequence of the present invention, an isolated protein or mimetope of the present invention, and/or an antibody of the present invention. The composition can also include an excipient, adjuvant, and/or carrier. Preferably, the therapeutic composition protects the animal against heartworm. The present invention also includes a method to protect an animal from parasitic helminth infection by administering such therapeutic compositions.

Yet another embodiment of the present invention includes a therapeutic composition capable of protecting an animal from parasitic helminth infection when administered to the animal in an effective manner, the composition including a compound capable of substantially interfering with the function of a parasitic helminth LDL receptor-related protein class A cysteine-rich motif. A preferred therapeutic composition is a protein encoded by an isolated nucleic acid sequence capable of hybridizing, under stringent conditions, to at least a portion of *Dirofilaria immitis* nucleic acid sequence p4. The present invention also includes a method to protect animals from parasitic helminth infection using such therapeutic compositions.

Preferred parasitic helminths of the present invention include nematodes, cestodes and trematodes, with filarial, ascarid, strongyle and trichostrongyle nematodes being more preferred. Dirofilaria, Onchocerca, Brugia, Wuchereria, Loa, Acanthocheilonema, Dipetalonema, Setaria, Parafilaria and Stephanofilaria filarial nematodes are even more preferred, and *Dirofilaria immitis*, the parasite that causes heartworm, is even more preferred.

DETAILED DESCRIPTION OF THE INVENTION

Figure 1:
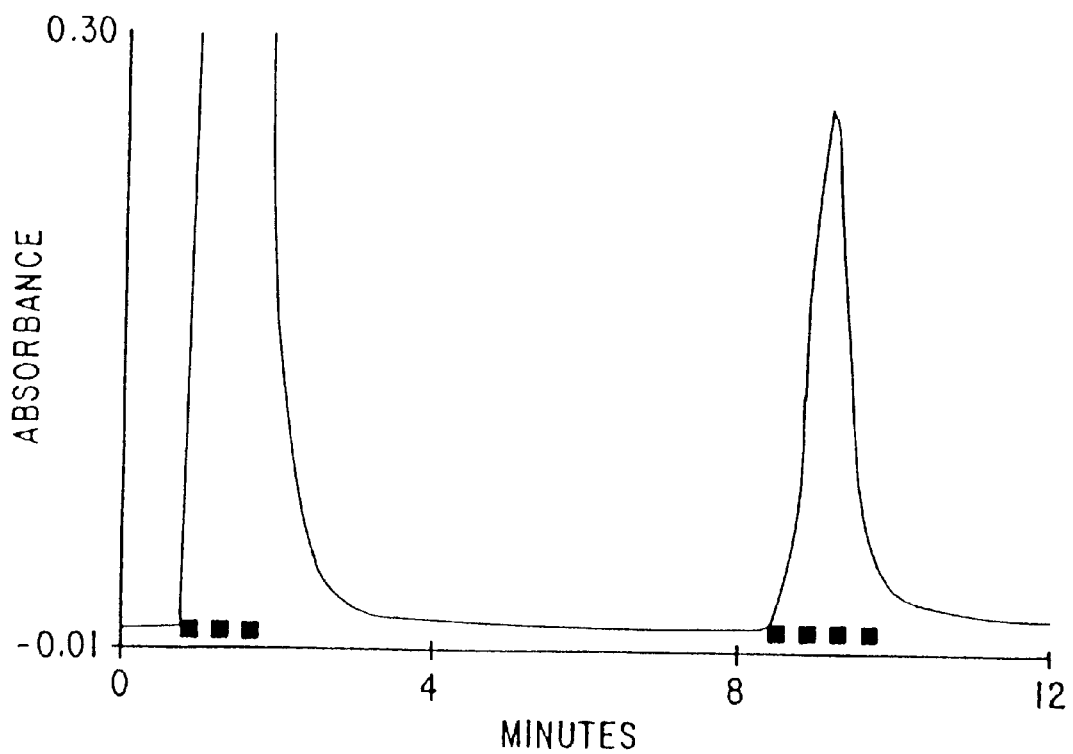
FIG. 1 depicts a chromatogram of the separation of larval ES by cation exchange chromatography.

The present invention includes isolated parasitic helminth proteins and mimetopes thereof that are capable of selectively binding to at least one component of a serum collected from an animal that is immune to infection by the helminth, the serum being capable of inhibiting helminth development. The ability of such proteins and mimetopes to selectively bind to components in such a serum is believed to suggest the ability of such proteins and mimetopes to protect an animal from parasite infection when such proteins and/or mimetopes are administered to an animal in an effective manner.

Animals that are immune to infection by parasitic helminths are animals that exhibit an immune response that is sufficient to protect the animal from such infection. Immune animals typically are animals that have been administered larval, adult and/or microfilarial helminths in a manner effective to elicit a protective response, preferably using irradiated helminths or a chemically-abbreviated infection protocol. For example, dogs receiving chemically abbreviated *D. immitis* larval infections exhibit significant immunity to challenge infections. Furthermore, sera obtained from such dogs are effective in passively transferring larval killing and stunting capabilities to mice. Preferred immune animals are those that have been immunized against helminth larvae, particularly against L3 and/or L4 larvae, since, in accordance with the present invention, it is particularly desirable to prevent L3 larvae introduced into an animal from developing into adult parasites. It should be noted, however, that immune animals do not preclude naturally-infected animals that generate protective antibodies.

According to the present invention, an isolated, or biologically pure, parasitic helminth protein, is a protein that has been removed from its natural milieu. As such, "isolated" and "biologically pure" do not necessarily reflect the extent to which the protein has been purified. An isolated parasitic helminth protein can be obtained from its natural source. Alternatively, the isolated parasitic helminth protein can be produced using recombinant DNA technology or chemical synthesis. Isolated proteins include full-length proteins as well as; modified versions of the protein in which amino acids have been deleted (e.g., a truncated version of the protein, such as a peptide), inserted, inverted, substituted and/or derivatized (e.g., glycosylated, phosphorylated, acetylated) such that the modified version of the protein has a biological function substantially similar to that of the natural protein (i.e., functionally equivalent to the natural protein). Modifications can be accomplished by techniques known in the art including, but not limited to, direct modifications to the protein or modifications to the gene encoding the protein using, for example, classic or recombinant DNA techniques to effect random or targeted mutagenesis. Isolated proteins of the present invention, including modified versions thereof, can be identified in a straight-forward manner by the proteins' ability to selectively bind to at least one component of anti-parasitic helminth immune serum. As used herein, immune serum refers to serum that is capable of inhibiting helminth development that preferably is derived (e.g., obtained from) an animal that is immune to the helminth. The minimum size of isolated proteins of the present invention is sufficient to form an epitope, a size that is typically at least about 7 to about 9 amino acids. As is appreciated by those skilled in the art, an epitope can include amino acids that naturally are contiguous to each other as well as amino acids that, due to the tertiary structure of the natural protein, are in sufficiently close proximity to form an epitope.

In accordance with the present invention, a mimetope refers to any compound that is able to mimic the ability of an isolated protein of the present invention to selectively bind to at least one component of anti-parasitic helminth immune serum. A mimetope can be a peptide that has been modified to decrease its susceptibility to degradation but that still retains its selective binding ability. Other examples of mimetopes include, but are not limited to, anti-idiotypic antibodies, or fragments thereof, that include at least one binding site that mimics one or more epitopes of an isolated protein; non-proteinaceous immunogenic portions of an isolated protein (e.g., carbohydrate structures); and synthetic or natural organic molecules, including nucleic acids, that have a structure similar to at least one epitope of an isolated protein of the present invention. Such mimetopes can be obtained, for example, by affinity chromatography techniques using immune sera of the present invention or antibodies raised against isolated proteins of the present invention.

As used herein, the term "selectively binds to" refers to the ability of isolated proteins and mimetopes thereof to bind to serum collected from animals that have been exposed to parasitic helminths (either through natural infection or through administration of helminths) but essentially not to bind, according to standard detection techniques (such as those described in Sambrook et al., *Molecular Cloning: A Laboratory Manual*, Cold Spring Harbor Labs Press, 1989, which is incorporated herein by reference in its entirety) to serum collected from animals that have not been exposed to parasitic helminths (i.e., naive animals). Preferably, the isolated proteins and mimetopes are able to bind to anti-parasitic helminth immune serum with high affinity. The ability of a protein or mimetope thereof to selectively bind to anti-parasitic helminth immune serum can be measured using a variety of methods known to those skilled in the art including immunoblot assays, immunoprecipitation assays, enzyme immunoassays (e.g., ELISA), radioimmunoassays, immunofluorescent antibody assays and immunoelectron microscopy. It should be noted that the ability of an isolated protein or mimetope thereof to selectively bind to immune serum raised against a certain stage of helminth development does not preclude the isolated protein or mimetope from being able to also bind to immune serum raised against other stages of helminth development. For example, the ability of an isolated protein or mimetope thereof to selectively bind to an anti-larval immune serum does not preclude the isolated protein or mimetope from being able to also bind to anti-microfilarial and/or anti-adult immune serum.

One embodiment of the present invention is the use of anti-parasitic helminth immune serum to identify isolated proteins and mimetopes of the present invention, a technique referred to herein as immune serum screening assay. Immune serum can be raised against a parasitic helminth by administering the helminth to an animal under conditions that elicit an immune response. Immune serum can be raised against larval, microfilarial, and/or adult helminths, preferably against larvae, and more preferably against L3 and/or L4 larvae. Immune sera of the present invention are capable not only of inhibiting development of the species of helminth that elicited the immune response, but also of helminth species that immunologically cross-react with the immune sera. Due to the similarity between helminths, immune sera of the present invention are capable of reacting with a large variety of helminths. Inhibiting the development of helminths includes killing, reducing the growth of, blocking the maturation of, altering the morphology of, altering the metabolism of, and/or otherwise being detrimental to the helminth.

Any animal that is capable of mounting an immune response to protect itself from helminth infection is a suitable animal to which helminths can be administered and from which immune serum can be collected. For example, a preferred animal from which to collect serum capable of inhibiting the development of *Dirofilaria immitis* is a dog that has been administered L3 and/or L4 *Dirofilaria immitis* larvae under conditions that elicit an immune response.

The ability of immune serum of the present invention to inhibit parasitic helminth development can be determined in a number of ways. A preferred method to monitor the ability of immune serum to inhibit the development of an infectious agent is disclosed in U.S. patent application Ser. No. 07/654, 226, referenced above. As disclosed therein, for example, the ability of an anti-parasitic helminth larval immune serum to inhibit larval development can be determined as follows. Briefly, a naive animal (i.e., an animal not previously exposed to parasitic helminth larvae) is implanted with at least one diffusion chamber containing helminth larvae, preferably L3 larvae. The animal is also administered either the anti-larval immune serum to be tested or a control non-immune serum, preferably at a site near the diffusion chambers. After a suitable period of time, for example, from about three to about four weeks for *Dirofilaria immitis* larvae implanted in mice, the diffusion chambers are removed, and the effects of the immune serum on larval growth and development are determined by, for example, comparing larval growth and survival in chambers exposed to anti-larval immune serum with the growth and survival of larvae in diffusion chambers exposed to non-immune serum. A significant number of larvae exposed to anti-larval immune serum are either killed or stunted compared to larvae exposed to non-immune serum.

U.S. patent application Ser. No. 07/654,226 further discloses use of the immune serum screening assay to screen for, and hence identify, desired proteins that selectively bind to the immune serum. Briefly, the immune serum can be contacted with a protein-containing composition under conditions that permit selective binding by desired proteins to components in the serum. Complexes between the proteins and serum components are recovered, the proteins are separated from the serum components and are then analyzed. Nucleic acid sequence encoding such proteins can be identified using known recombinant DNA techniques, such as those described in Sambrook et al., ibid. In another embodiment, the immune serum screening assay can be used to identify nucleic acid sequences encoding isolated proteins of the present invention by screening parasite helminth expression cDNA libraries with immune sera of the present invention to identify proteins expressed by individual clones that are capable of selectively binding to the immune sera. The immune serum screening assay can also be used to identify mimetopes capable of selectively binding to immune serum, such as to anti-L3 and/or L4 larval immune serum. Mimetopes can also be designed or improved using information derived from proteins identified by the immune serum screening assay. It should be appreciated that not only serum, but also other immunogenic components of bodily fluids collected from animals immune to helminth infection, such as cells, specific antibodies, and fragments thereof, can be used in the immune serum screening assay.

As disclosed in U.S. patent application Ser. No. 07/654, 226, anti-larval immune serum has been used to identify nematode proteins expressed during L3 and/or L4 that have molecular weights of 66 kD, 65 kD, 59 kD, 39 kD, 33 kD, 23/24 kD, 22/20.5 kD and 14 kD, as determined by their migration patterns when submitted to Tris-glycine SDS PAGE. Nucleic acid sequences encoding these proteins can be identified using anti-L3 and/or L4 larval immune serum to screen larval nematode cDNA expression libraries. U.S. application Ser. No. 08/003,257, referenced above, discloses 22-kD and 20.5-kD nematode proteins (sizes determined by Tris glycine SDS-PAGE), referred to herein as P22L and P20.5, and nucleic acid sequences that encode them, herein referred to as p22L and p20.5. P22L and P20.5 are the same protein except that P22L has a hydrophobic leader sequence attached to the P20.5 protein. U.S. application Ser. No. 08/003,389, referenced above, discloses 39-kD nematode proteins (sizes determined by Tris glycine SDS-PAGE), referred to herein as P39, and nucleic acid sequences that encode them, herein referred to as p39. The present application, by incorporating U.S. application Ser. Nos. 07/654,226, 08/003,257 and 08/003,389 by reference herein in their entireties, includes *D. immitis* P22L, *D. immitis* P20.5, *D. immitis* P39, additional parasitic helminth proteins sharing significant homology with *D. immitis* P22L, *D. immitis* P20.5, or *D. immitis* P39, nucleic acid sequences encoding any of these proteins, mimetopes of these proteins, and antibodies that selectively bind to any of these proteins, as well as uses of these proteins, mimetopes, nucleic acid sequences, and antibodies.

One embodiment of the present invention is an isolated parasitic helminth nucleic acid sequence that encodes an isolated protein of the present invention. As used herein, an isolated parasitic helminth nucleic acid sequence is a nucleic acid sequence that has been removed from its natural milieu. As such, "isolated" does not reflect the extent to which the nucleic acid sequence has been purified. An isolated nucleic acid sequence can be DNA, RNA, or derivatives of either DNA or RNA. Isolated nucleic acid sequences of the present invention include sequences that encode at least one epitope capable of selectively binding to immune sera of the present invention as well as oligonucleotides that can function in a variety of ways, including, but not limited to, as probes, primers, and therapeutic agents using, for example, antisense-, triplex formation- and/or ribozyme-based technologies. An isolated parasitic helminth nucleic acid sequence can be obtained from its natural source either as an entire gene or a portion thereof, the minimal size of a portion being a size that can form a stable hybrid with a similar nucleic acid sequence under stringent conditions. As such, isolated nucleic acid sequences can include regulatory regions that control expression of the corresponding coding region (e.g., transcription or translation control regions), full-length or partial coding regions, and combinations thereof. Isolated parasitic helminth nucleic acid sequences can also be produced using recombinant DNA technology (e.g., PCR amplification, cloning) or chemical synthesis. Isolated parasitic helminth nucleic acid sequences include functional equivalents of natural sequences, including, but not limited to, natural allelic variants and modified nucleic acid sequences in which nucleotides have been inserted, deleted, substituted, and/or inverted in such a manner that such modifications do not substantially interfere with the nucleic acid sequence's ability to encode an epitope recognized by immune sera of the present invention or do not substantially interfere with the ability of the nucleic acid sequence to form stable hybrids under stringent conditions with natural isolates. As used herein, stringent hybridization conditions refer to standard hybridization conditions under which nucleic acid sequences, including oligonucleotides, are used to identify similar sequences. Such standard conditions are disclosed, for example, in Sambrook et al., ibid. Examples of such conditions are provided in the Examples section.

Functionally equivalent nucleic acid sequences can be obtained using methods known to those skilled in the art (see, for example, Sambrook et al., ibid.). For example, nucleic acid sequences can be modified using a variety of techniques including, but not limited to, classic mutagenesis techniques and recombinant DNA techniques, such as site-directed mutagenesis, chemical treatment of a nucleic acid to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid sequences, and combinations thereof. Functionally equivalent nucleic acids can be selected from a mixture of modified nucleic acid sequences by screening for the function of the protein encoded by the nucleic acid sequence (e.g., ability to bind to immune serum) and/or by hybridization with natural nucleic acid sequences under stringent conditions.

Due to the similarity between parasitic helminth genomes, isolated proteins and corresponding nucleic acid sequences of the present invention can be from any parasitic helminth. Preferred helminths include nematode, cestode and trematode parasites. More preferred helminths include filarial, ascarid, strongyle and trichostrongyle nematodes. Even more preferred helminths include Dirofilaria, Onchocerca, Brugia, Wuchereria, Loa, Acanthocheilonema, Dipetalonema, Setaria, Parafilaria and Stephanofilaria filarial nematodes. A particularly preferred parasitic helminth of the present invention is *Dirofilaria immitis*, the filarial nematode that causes heartworm.

One embodiment of the present invention is an isolated parasitic helminth nucleic acid sequence that is capable of hybridizing, under stringent conditions, to at least a portion of *D. immitis* nucleic acid sequence p4. A protein encoded by such a nucleic acid sequence is preferably capable of selectively binding to at least one component of anti-parasitic helminth immune serum, and more preferably to anti-L3 and/or L4 larval immune serum. *D. immitis* nucleic acid sequence p4, also referred to as *D. immitis* p4, is a nucleic acid sequence of about 913 nucleotides in length that has been isolated from a *D. immitis* L3 and/or L4 cDNA expression library using immune serum collected from a dog that was immunized by repeated chemically abbreviated infections (e.g., infect with about 200 L3, wait about 60 days, treat with ivermectin, wait about 60 days, reinfect, etc.). Sequencing of *D. immitis* p4 has resulted in the nucleic acid sequence disclosed in SEQ ID NO:1. It should be noted that sequencing technology is not entirely error-free and that SEQ ID NO:1, as such, represents an apparent nucleic acid sequence of *D. immitis* p4. The deduced translation of SEQ ID NO:1, represented in SEQ ID NO:2, suggests that *D. immitis* p4 comprises an open reading frame of about 303 amino acids and, as such, represents only a portion of the entire coding sequence of the gene. The nucleic acid contained in *D. immitis* p4, however, is sufficient to encode a protein that selectively binds with anti-*D. immitis* larval immune serum, as demonstrated by the manner in which the nucleic acid sequence was isolated. The deduced translation of SEQ ID NO:1 suggests that the protein encoded by *D. immitis* p4 has a molecular weight of about 35.5 kilodaltons (kD) and an estimated pI of 4.26.

The protein encoded by *D. immitis* p4 is further characterized by having an LDL receptor-related protein (LDLr) class A cysteine-rich motif of about 9 amino acids that is also found in several other proteins, including mammalian low density lipoprotein (LDL) receptors, LDL receptor-related proteins, human and mouse alpha-2-macroglobulin receptors and rat renal GP 330 glycoprotein. Each of these proteins, including *D. immitis* P4, share the sequence DDCGDGSDE, set forth in SEQ ID NO:5 (i.e., Aspartic Acid—Aspartic Acid cysteine—Glycine—Aspartic Acid—Glycine—Serine—Aspartic Acid—Glutamic Acid). A conserved stretch of eight of the nine amino acids is also found in the free-living (i.e., non-parasitic) nematode *Caenorhabditis elegans* LDL receptor-related protein and *C. elegans* basement membrane proteoglycan. This LDLr class A, cysteine-rich motif is likely to be conserved in proteins encoded by p4-related sequences of other helminths (i.e., nucleic acid sequences that hybridize under stringent conditions with *D. immitis* p4). As such, p4-related nucleic acid sequences may be identified using oligonucleotide probes that encode such LDLr class A motifs. Furthermore, the LDLr class A motif in P4-related proteins represents a target for development of therapeutic compositions to protect animals from parasitic helminth infection, as discussed below.

The present invention includes nucleic acid sequences from any parasitic helminth that hybridize under stringent conditions to at least a portion of *D. immitis* nucleic acid sequence p4, the minimal size of the portion being defined by the hybridization conditions. Due to the similarities between parasitic helminths, as heretofore disclosed, one can use *D. immitis* p4 sequences to obtain other parasitic helminth nucleic acid sequences that are capable of hybridizing, under stringent conditions, to at least a portion of *D. immitis* p4. Preferred helminths are heretofore disclosed.

Particularly preferred nucleic acid sequences of the present invention include *D. immitis* nucleic acid sequence p4, nucleic acid sequences including *D. immitis* p4, and nucleic acid sequence comprising fragments of *D. immitis* p4 (including functional equivalents of any of these nucleic acid sequences). Knowing the sequence of *D. immitis* p4 allows one skilled in the art to make copies of the sequence as well as to obtain nucleic acid sequences including *D. immitis* p4 and nucleic acid sequences that contain fragments of *D. immitis* p4. As such, particularly preferred isolated nucleic acid sequences include SEQ ID NO:1 or a functional equivalent thereof, a nucleic acid sequence containing at least a portion of SEQ ID NO:1 or a functional equivalent thereof, and a fragment of SEQ ID NO:1 or a functional equivalent thereof, assuming the accuracy of SEQ ID NO:1.

The present invention also includes an isolated parasitic helminth protein that is encoded, at least in part, by a parasitic helminth nucleic acid sequence capable of hybridizing, under stringent conditions, to at least a portion of *D. immitis* nucleic acid sequence p4, as well as mimetopes of such a protein. Preferably, the protein or mimetope thereof is also capable of selectively binding to at least one component of anti-parasitic helminth immune serum, and more preferably to anti-L3 and/or L4 larval immune serum. Preferred isolated parasitic helminth proteins or mimetopes thereof are capable of protecting an animal from helminth infection when administered to the animal in an effective manner. Preferred helminths are heretofore disclosed. Particularly preferred isolated proteins include proteins encoded by *Dirofilaria immitis* nucleic acid sequence p4, a nucleic acid sequence including *D. immitis* p4, or a nucleic acid sequence comprising a fragment of *D. immitis* p4. As such, particularly preferred isolated proteins are those encoded by SEQ ID NO:1 or a functional equivalent thereof, a nucleic acid sequence containing at least a portion of SEQ ID NO:1 or a functional equivalent thereof, and a fragment of SEQ ID NO:1 or a functional equivalent thereof, as well as proteins that contain at least a portion of SEQ ID NO:2, assuming the accuracy of SEQ ID NO:1 and SEQ ID NO:2.

One embodiment of the present invention is an isolated parasitic helminth nucleic acid sequence that is capable of hybridizing, under stringent conditions, to at least a portion of *D. immitis* nucleic acid sequence p22U. A protein encoded by such a nucleic acid sequence is preferably capable of selectively binding to at least one component of anti-parasitic helminth immune serum, and more preferably to anti-L3 and/or L4 larval immune serum. *D. immitis* nucleic acid sequence p22U, also referred to as *D. immitis* p22U, encodes at least a substantial portion of a basic *D. immitis* protein, referred to as *D. immitis* P22U protein, that migrates at an apparent molecular weight of about 22 kD when submitted to Tris-glycine SDS (sodium dodecyl sulfate) PAGE (polyacrylamide gel electrophoresis). *D. immitis* P22U protein has been identified in larval ES (excretory-secretory) extracts as well as in extracts of L3, L4 and adults. *D. immitis* p22U is about 1016 nucleotides in length. Sequencing of *D. immitis* p22U has resulted in the nucleic acid sequence disclosed in SEQ ID NO:3. It should be noted that sequencing technology is not entirely error-free and that SEQ ID NO:3, as such, represents an apparent nucleic acid sequence of *D. immitis* p22U. The deduced translation of SEQ ID NO:3, represented in SEQ ID NO:4, suggests that *D. immitis* p22U includes an open reading frame of about 208 amino acids followed by a stop codon. The translation start site is as yet unknown although there are two "in-frame" potential start codons at about amino acid 13 and about amino acid 19 of corresponding (i.e., deduced) amino acid sequence SEQ ID NO:4. The deduced amino acid sequence suggests a protein having a molecular weight of about 22 kD and an estimated pI of about 9.6.

*D. immitis* p22U can be isolated in a number of ways including, but not limited to, screening an L3, L4, or adult expression cDNA library with appropriate immune serum or with antibodies raised against *D. immitis* P22U protein. Alternatively, amino acid sequence information can be derived from purified *D. immitis* P22U protein that can be used to design oligonucleotide probes and/or primers that can be used to screen and/or amplify sequences from an appropriate cDNA or genomic library.

The present invention includes nucleic acid sequences from any parasitic helminth that hybridize under stringent conditions to at least a portion of *D. immitis* nucleic acid sequence p22U, the minimal size of the portion being defined by the hybridization conditions. Due to the similarities between parasitic helminths, as heretofore disclosed, one can use *D. immitis* p22U to obtain other parasitic helminth nucleic acid sequences that are capable of hybridizing, under stringent conditions, to at least a portion of *D. immitis* p22U. Preferred helminths are heretofore disclosed.

Particularly preferred p22U-related nucleic acid sequences of the present invention include *Dirofilaria immitis* nucleic acid sequence p22U, nucleic acid sequences including *D. immitis* p22U, and nucleic acid sequence comprising fragments of *D. immitis* p22U (including functional equivalents of each of these nucleic acid sequences). Knowing the sequence of *D. immitis* p22U allows one skilled in the art to make copies of the sequence as well as to obtain nucleic acid sequences including *D. immitis* p22U and nucleic acid sequences that contain fragments of *D. immitis* p22U. As such, particularly preferred isolated nucleic acid sequences include SEQ ID NO:3 or a functional equivalent thereof, a nucleic acid sequence containing at least a portion of SEQ ID NO:3 or a functional equivalent thereof, and a fragment of SEQ ID NO:3 or a functional equivalent thereof, assuming the accuracy of SEQ ID NO:3.

The present invention also includes an isolated parasitic helminth protein that is encoded, at least in part, by a parasitic helminth nucleic acid sequence capable of hybridizing, under stringent conditions, to at least a portion of D. immitis nucleic acid sequence p22U, as well as mimetopes of such a protein. Preferably, the protein or mimetope thereof is also capable of selectively binding to at least one component of anti-parasitic helminth immune serum, and more preferably to anti-L3 and/or L4 larval immune serum. Preferred isolated parasitic helminth proteins or mimetopes thereof are capable of protecting an animal from helminth infection when administered to the animal in an effective manner. Preferred helminths are heretofore disclosed. Particularly preferred isolated proteins include proteins encoded by Dirofilaria immitis nucleic acid sequence p22U, a nucleic acid sequence including D. immitis p22U, or a nucleic acid sequence comprising a fragment of D. immitis p22U. As such, particularly preferred isolated proteins are those encoded by SEQ ID NO:3 or a functional equivalent thereof, a nucleic acid sequence containing at least a portion of SEQ ID NO:3 or a functional equivalent thereof, and a fragment of SEQ ID NO:3 or a functional equivalent thereof, as well as proteins that contain at least a portion of SEQ ID NO:4, assuming the accuracy of SEQ ID NO:3 and SEQ ID NO:4.

Isolated nucleic acid sequences of the present invention can also include a nucleic acid that is capable of hybridizing, under stringent conditions, to at least a portion of both D. immitis nucleic acid sequence p4 and D. immitis nucleic acid sequence p22U. Such a nucleic acid sequence can encode a protein including portions of both P4 and P22U. Alternatively, such a nucleic acid sequence could encode both a P4-related and a P22-related protein.

The present invention also includes oligonucleotides that are capable of hybridizing, under stringent conditions, to complementary regions of other, preferably longer, nucleic acid sequences of the present invention, such as to complementary regions of D. immitis nucleic acid sequence p4, complementary regions of nucleic acid sequences that include at least a portion of D. immitis p4, complementary region of nucleic acid sequences that hybridize under stringent conditions to D. immitis p4, complementary regions of D. immitis nucleic acid sequence p22U, complementary regions of nucleic acid sequences that include at least a portion of D. immitis p22U, and complementary regions of nucleic acid sequences that hybridize under stringent conditions to D. immitis p22U. The oligonucleotides can be RNA, DNA, or derivatives of either. The minimal size of such oligonucleotides is the size required to form a stable hybrid between a given oligonucleotide and the complementary sequence on another nucleic acid sequence of the present invention. As such, the size is dependent on nucleic acid composition and percent homology between the oligonucleotide and complementary sequence as well as upon hybridization conditions per se (e.g., temperature, salt concentration). For AT-rich nucleic acid sequences, such as those of D. immitis, oligonucleotides typically are at least about 15 to about 17 bases in length. The size of the oligonucleotide must also be sufficient for the use of the oligonucleotide in accordance with the present invention. Oligonucleotides of the present invention can be used in a variety of applications including, but not limited to, as probes to identify additional nucleic acid sequences, as primers to amplify or extend nucleic acid sequences, or in therapeutic applications to inhibit, for example, expression of nucleic acid sequences into parasitic helminth proteins that are important in the life cycle of the parasite. Such therapeutic applications include the use of such oligonucleotides in, for example, antisense-, triplex formation-, and/or ribozyme-based technologies.

Isolated nucleic acid sequences of the present invention, such as nucleic acid sequences that hybridize under stringent conditions with either D. immitis p4 or D. immitis p22U, can be obtained in a variety of ways. For example, an isolated nucleic acid sequence of the present invention can be obtained by a method that includes induction of a L3 and/or L4 expression library under conditions that promote production of larval proteins encoded by the library; contacting the library with immune serum collected from an animal that is immune to infection by L3 and/or L4; and selecting a colony or phage plaque that contains a nucleic acid sequence encoding a protein capable of selectively binding to the serum. Conventional culturing and selection methods are taught, for example, in Sambrook et al., ibid. An example of this methodology is also provided in the Examples section.

In another embodiment, an isolated nucleic acid sequence is obtained by a method including contacting, under stringent hybridization conditions, at least one oligonucleotide with a parasitic helminth cDNA library, such that the oligonucleotide includes nucleic acid sequences that encode at least a portion of D. immitis P4 and/or D. immitis P22U; and selecting a colony or phage plaque having a nucleic acid sequence that hybridizes under stringent conditions with the oligonucleotide. Alternatively, oligonucleotide primers, including nucleic acid sequences that encode at least portions of D. immitis P4 and/or D. immitis P22U, can be used to amplify, by polymerase chain reaction (PCR) amplification, nucleic acid sequences that include at least a portion of D. immitis p4 and/or D. immitis p22U. An example of these methodologies is provided in the Examples section.

In yet another embodiment, an isolated nucleic acid sequence is obtained by a method including contacting a collection of nucleic acid sequences, such as a parasitic helminth cDNA library, with D. immitis p4 or a portion thereof, or with D. immitis p22U or a portion thereof, under stringent hybridization conditions; and identifying a nucleic acid sequence that hybridizes to either D. immitis p4 or the portion thereof, or with D. immitis p22U or the portion thereof, under such conditions. Such a technique can be used to clone a nucleic acid sequence using standard hybridization techniques or to amplify a nucleic acid sequence using PCR amplification. Alternatively, serum raised against D. immitis P4 or D. immitis P22U could be used to screen cDNA expression libraries.

The present invention also includes recombinant vectors, which include a parasitic helminth nucleic acid sequence of the present invention inserted into any vector capable of delivering the nucleic acid into a host cell. The vector contains heterologous nucleic acid sequences, that is nucleic acid sequences that are not naturally found adjacent to parasitic helminth nucleic acid sequences of the present invention and that preferably are derived from a species other than the species from which the parasitic helminth nucleic acid sequences are derived. The vector can be either RNA or DNA, either prokaryotic or eukaryotic, and typically is a virus or a plasmid. Recombinant vectors can be used in the cloning, sequencing, and/or otherwise manipulating of nucleic acid sequences of the present invention. One type of recombinant vector, herein referred to as a recombinant molecule and described in more detail below, can be used in the expression of nucleic acid sequences of the present invention. Preferred recombinant vectors are capable of replicating in the transformed cell. Preferred nucleic acid sequences to include in recombinant vectors of the present invention include parasitic helminth nucleic acid sequences capable of hybridizing, under stringent conditions, to at least a portion of *Dirofilaria immitis* nucleic acid sequence p4 or to at least a portion of *Dirofilaria immitis* nucleic acid sequence p22U. Particularly preferred nucleic acid sequences with which to transform cells include *D. immitis* nucleic acid sequence p4, nucleic acid sequences including *D. immitis* p4, nucleic acid sequence comprising fragments of *D. immitis* p4, *D. immitis* nucleic acid sequence p22U, nucleic acid sequences including *D. immitis* p22U, and nucleic acid sequence comprising fragments of *D. immitis* p22U.

Isolated proteins of the present invention can be produced in a variety of ways, including production and recovery of natural proteins, production and recovery of recombinant proteins, and chemical synthesis. In one embodiment, an isolated protein of the present invention is produced by culturing a cell capable of expressing the protein under conditions effective to produce said protein, and recovering the protein. A preferred cell to culture is a recombinant cell that is capable of expressing the protein, the recombinant cell being produced by transforming a host cell with one or more nucleic acid sequences of the present invention. Transformation of a nucleic acid sequence into a host cell can be accomplished by any method by which a nucleic acid sequence can be inserted into a cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid sequences of the present invention can remain extrachromosomal or can integrate into one or more sites within a chromosome of a host cell in such a manner that their ability to be expressed is retained. Preferred nucleic acid sequences with which to transform cells include parasitic helminth nucleic acid sequences capable of hybridizing, under stringent conditions, to at least a portion of *Dirofilaria immitis* nucleic acid sequence p4 or to at least a portion of *Dirofilaria immitis* nucleic acid sequence p22U. Particularly preferred nucleic acid sequences with which to transform cells include *D. immitis* nucleic acid sequence p4, nucleic acid sequences including *D. immitis* p4, nucleic acid sequence comprising fragments of *D. immitis* p4, *D. immitis* nucleic acid sequence p22U, nucleic acid sequences including *D. immitis* p22U, and nucleic acid sequence comprising fragments of *D. immitis* p22U.

Suitable host cells to transform include any cell that can be transformed. Host cells can be either untransformed cells or cells that are already transformed with at least one nucleic acid sequence. Host cells of the present invention either can be endogenously (i.e., naturally) capable of producing isolated proteins of the present invention or can be capable of producing such proteins after being transformed with at least one nucleic acid sequence of the present invention. Host cells of the present invention can be any cell capable of producing an isolated protein of the present invention, including bacterial, yeast, other fungal, insect, animal, and plant cells. Preferred host cells include bacterial, mycobacterial, yeast, insect and mammalian cells, and more preferred host cells include Salmonella, Escherichia, Bacillus, Saccharomyces, Spodoptera, Mycobacteria, Trichoplusia, BHK (baby hamster kidney) cells, MDCK cells (normal dog kidney cell line for canine herpesvirus cultivation), CRFK cells (normal cat kidney cell line for feline herpesvirus cultivation) and COS cells. Particularly preferred host cells are *Escherichia coli*, including *E. coli* K-12 derivatives; *Salmonella typhi*; *Salmonella typhimurium*, including attenuated strains such as UK-1 $\chi$3987 and SR-11 $\chi$4072; *Spodoptera frugiperda*; *Trichoplusia ni*; MDCK cells; and CRFK cells.

A recombinant cell is preferably produced by transforming a host cell with one or more recombinant molecules, each comprising one or more nucleic acid sequences of the present invention operatively linked to an expression vector containing one or more transcription control sequences. A cell can be transformed with one or more recombinant molecules. The phrase operatively linked refers to insertion of a nucleic acid sequence into an expression vector in a manner such that the sequence is able to be expressed when transformed into a host cell. As used herein, an expression vector is a DNA or RNA vector that is capable of transforming a host cell, of replicating within the host cell, and of effecting expression of a specified nucleic acid sequence. Expression vectors can be either prokaryotic or eukaryotic, and are typically viruses or plasmids. Expression vectors of the present invention include any vectors that function (i.e.,direct gene expression) in recombinant cells of the present invention, including in bacterial, yeast, other fungal, insect, animal, and plant cells. Preferred expression vectors of the present invention can direct gene expression in bacterial, yeast, insect and mammalian cells and more preferably in the cell types heretofore disclosed.

Expression vectors of the present invention may also contain secretory signals to enable an expressed parasitic helminth protein to be secreted from its host cell or may contain fusion sequences which lead to the expression of inserted nucleic acid sequences of the present invention as fusion proteins. Eukaryotic recombinant molecules may include intervening and/or untranslated sequences surrounding and/or within parasitic helminth nucleic acid sequences.

Nucleic acid sequences of the present invention can be operatively linked to expression vectors containing regulatory sequences such as promoters, operators, repressors, enhancers, termination sequences, origins of replication, and other regulatory sequences that are compatible with the host cell and that control the expression of the nucleic acid sequences. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, helminths, helminth cells, insect and mammalian cells, such as, but not limited to, tac, lac, trp, trc, oxy-pro, bacteriophage lambda (such as lambda $p_L$ and lambda $p_R$), bacteriophage T7, T7lac, bacteriophage T3, bacteriophage SP6, bacteriophage SP01, metallothionein, alpha mating factor, Pichia alcohol oxidase, alphavirus subgenomic promoters (such as Sindbis virus subgenomic promoters), baculovirus, *Heliothis zea* insect virus, vaccinia virus, adenovirus, simian virus 40, retrovirus actin, heat shock, phosphate and nitrate transcription control sequences as well as other sequences capable of controlling gene expression in prokaryotic or eukaryotic cells. Transcription control sequences of the present invention can also include naturally occurring transcription control sequences previously associated with a nucleic acid sequence prior to isolation.

A recombinant molecule of the present invention can be any nucleic acid sequence heretofore described operatively linked to any transcription control sequence capable of effectively regulating expression of the nucleic acid sequence in the cell to be transformed. Preferred recombinant molecules include parasitic helminth nucleic acid sequences capable of hybridizing, under stringent conditions, to at least a portion of *Dirofilaria immitis* nucleic acid sequence p4 or to at least a portion of *Dirofilaria immitis* nucleic acid sequence p22U. Particularly preferred recombinant molecules contain *D. immitis* nucleic acid sequence p4, nucleic acid sequences including *D. immitis* p4, nucleic acid sequence comprising fragments of *D. immitis* p4, *D. immitis* nucleic acid sequence p22U, nucleic acid sequences including *D. immitis* p22U, and nucleic acid sequence comprising fragments of *D. immitis* p22U. Even more preferred recombinant molecules include pβgal-p4, pHis-p4, pET19b-p4$_{635}$, pβgal-p22U, pHis-p22U, and pHis-p22U$_{608}$.

Recombinant cells of the present invention include any cells transformed with any nucleic acid sequences of the present invention. Preferred recombinant cells are transformed with recombinant molecules containing at least one of the following: a parasitic helminth nucleic acid sequence capable of hybridizing, under stringent conditions, to at least a portion of *Dirofilaria immitis* nucleic acid sequence p4 or a parasitic helminth nucleic acid sequence capable of hybridizing, under stringent conditions, to at least a portion of *Dirofilaria immitis* nucleic acid sequence p22U. More preferred recombinant cells are transformed with recombinant molecules including *D. immitis* nucleic acid sequence p4, nucleic acid sequences including *D. immitis* p4, nucleic acid sequence comprising fragments of *D. immitis* p4, *D. immitis* nucleic acid sequence p22U, nucleic acid sequences including *D. immitis* p22U, and/or nucleic acid sequence comprising fragments of *D. immitis* p22U. Such recombinant cells can also be co-transformed with recombinant molecules including nucleic acid sequences encoding other helminth parasitic proteins, such as *D. immitis* P39, *D. immitis* P22L, *D. immitis* P20.5, *D. immitis* Di22, and *D. immitis* proteases expressed in L3 and/or L4 larvae, as well as other helminth proteins sharing significant homology with *D. immitis* P39, *D. immitis* P22L, *D. immitis* P20.5, *D. immitis* Di22 and *D. immitis* proteases expressed in L3 and/or L4 larvae. Di22 is disclosed in a File Wrapper Continuation, filed May 10, 1993, of U.S. patent application Ser. No. 07/683,202, filed Apr. 8, 1991, entitled "Heartworm Vaccine", which is incorporated by reference herein in its entirety. The protease is disclosed in U.S. patent application Ser. No. 07/792,209 filed Nov. 12, 1991, entitled "Protease Vaccine Against Heartworm", which is incorporated by reference herein in its entirety. Particularly preferred recombinant cells include *E. coli*:pβgal-p4, *E. coli*:pHis-p4, *E. coli*:pET19b-p4$_{635}$, *E. coli*:pβgal-p22U, *E. coli*:pHis-p22U and *E. coli*:pHis-p22U$_{608}$.

It may be appreciated by one skilled in the art that use of recombinant DNA technologies can improve expression of transformed nucleic acid sequences by manipulating, for example, the number of copies of the nucleic acid sequences within a host cell, the efficiency with which those nucleic acid sequences are transcribed, the efficiency with which the resultant transcripts are translated, and the efficiency of post-translational modifications. Recombinant techniques useful for increasing the expression of nucleic acid sequences of the present invention include, but are not limited to, operatively linking nucleic acid sequences to high-copy number plasmids, integration of the nucleic acid sequences into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid sequences of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid sequences encoding such a protein.

In accordance with the present invention, recombinant cells can be used to produce at least one parasitic helminth protein of the present by culturing such cells under conditions effective to produce such a protein, and recovering the protein. Effective conditions to produce a protein include, but are not limited to, appropriate media, bioreactor, temperature, pH and oxygen conditions that permit protein production. An appropriate medium refers to any medium in which a cell of the present invention, when cultured, is capable of producing parasitic helminth proteins. An effective medium is typically an aqueous medium comprising assimilable carbohydrate, nitrogen and phosphate sources, as well as appropriate salts, minerals, metals and other nutrients, such as vitamins. The medium may comprise complex nutrients or may be a defined minimal medium. Cells of the present invention can be cultured in conventional fermentation bioreactors, which include, but are not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art. Examples of suitable conditions are included in the Examples section.

Depending on the vector and host system used for production, resultant proteins may either remain within the recombinant cell; be secreted into the fermentation medium; be secreted into a space between two cellular membranes, such as the periplasmic space in *E. coli*; or be retained on the outer surface of a cell or viral membrane. The phrase "recovering the protein" refers simply to collecting the whole fermentation medium containing the protein and need not imply additional steps of separation or purification. Parasitic helminth proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, chromatofocusing and differential solubilization. Isolated parasitic helminth proteins are preferably retrieved in "substantially pure" form. As used herein, "substantially pure" refers to a purity that allows for the effective use of the protein as a therapeutic composition or diagnostic. A vaccine for animals, for example, should exhibit no substantial toxicity and should be capable of stimulating the production of antibodies in a vaccinated animal.

One embodiment of the present invention is the expression of a parasitic helminth protein as a fusion protein which includes the parasitic helminth protein attached to a fusion segment. Such a fusion segment often aids in protein purification, such as permitting one to purify the resultant fusion protein using affinity chromatography. Fusion proteins can be produced by culturing a recombinant cell transformed with a fusion nucleic acid sequence that encodes a protein including the fusion segment attached to either the carboxyl and/or amino terminal end of the parasitic helminth protein. Preferred fusion segments include, but are not limited to, glutathione-S-transferase, β-galactosidase, a poly-histidine segment capable of binding to a divalent metal ion, maltose binding protein and immunoglobulin binding domains (e.g., protein A or portions thereof) with a poly-histidine segment being more preferred. Examples of fusion proteins of the present invention include PβGAL-P4, PHIS-P4, PHIS-P4$_{635}$, PβGAL-P22U, PHIS-P22U and PHIS-P22U$_{608}$.

The present invention also includes antibodies capable of selectively binding to a parasitic helminth protein or mimetope thereof, the protein or mimetope thereof being capable of selectively binding to at least one component of anti-parasitic helminth immune serum. Such antibodies can be either polyclonal or monoclonal antibodies. Antibodies of the present invention include functional equivalents such as antibody fragments and genetically-engineered antibodies, including single chain antibodies, that are capable of selectively binding to at least one of the epitopes of the protein or mimetope used to obtain the antibodies. Preferred antibodies are raised in response to proteins, or mimetopes thereof, that are encoded, at least in part, by a nucleic acid sequence capable of hybridizing, under stringent conditions, to at least a portion of *Dirofilaria immitis* nucleic acid sequence p4 or to at least a portion of *Dirofilaria immitis* nucleic acid sequence p22U.

A preferred method to produce antibodies of the present invention includes administering to an animal an effective amount of an isolated protein or mimetope thereof to produce the antibody, wherein the protein is capable of selectively binding to at least one component of serum from an animal that is immune to infection by the helminth, the serum being capable of inhibiting helminth development; and recovering the antibodies. Preferably the protein is encoded, at least in part, by a parasitic helminth nucleic acid sequence capable of hybridizing, under stringent conditions, to at least a portion of *Dirofilaria immitis* nucleic acid sequence p4 or by a parasitic helminth nucleic acid sequence capable of hybridizing, under stringent conditions, to at least a portion of *Dirofilaria immitis* nucleic acid sequence p22U. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as vaccines to passively immunize an animal in order to protect the animal from parasitic helminth infections, (b) as reagents in assays to detect parasitic helminth infection, and/or (c) as tools to recover desired parasitic helminth proteins from a mixture of proteins and other contaminants.

Furthermore, antibodies of the present invention can be used to target cytotoxic agents to parasitic helminths in order to directly kill helminths expressing proteins selectively bound by the antibodies. Targeting can be accomplished by conjugating (i.e., stably joining) such antibodies to the cytotoxic agents. Suitable cytotoxic agents include, but are not limited to: double-chain toxins (i.e., toxins having A and B chains), such as diphtheria toxin, ricin toxin, Pseudomonas exotoxin, modeccin toxin, abrin toxin, and shiga toxin; single-chain toxins, such as pokeweed antiviral protein, α-amanitin, and ribosome inhibiting proteins; and chemical toxins, such as melphalan, methotrexate, nitrogen mustard, doxorubicin and daunomycin. Preferred double-chain toxins are modified to include the toxic domain and translocation domain of the toxin but lack the toxin's intrinsic cell binding domain.

One embodiment of the present invention is a therapeutic composition capable of protecting an animal from parasitic helminth infection when administered to the animal in an effective manner. Such a composition includes at least one of the following protective compounds: (a) an isolated parasitic helminth protein, or mimetope thereof, capable of selectively binding to at least one component of an anti-parasitic helminth immune serum such that the protein is preferably encoded, at least in part, by a nucleic acid sequence capable of hybridizing, under stringent conditions, to at least a portion of *D. immitis* nucleic acid sequence p4; (b) an isolated parasitic helminth protein, or mimetope thereof, capable of selectively binding to at least one component of an anti-parasitic helminth immune serum such that the protein is preferably encoded, at least in part, by a nucleic acid sequence capable of hybridizing, under stringent conditions, to at least a portion of *D. immitis* nucleic acid sequence p22U; (c) an antibody capable of selectively binding to a parasitic helminth protein or mimetope thereof, that is capable of selectively binding to at least one component of an anti-parasitic helminth immune serum such that the protein is preferably encoded, at least in part, by a nucleic acid sequence capable of hybridizing, under stringent conditions, to at least a portion of *D. immitis* nucleic acid sequence p4; (d) an antibody capable of selectively binding to a parasitic helminth protein or mimetope thereof, that is capable of selectively binding to at least one component of an anti-parasitic helminth immune serum such that the protein is preferably encoded, at least in part, by a nucleic acid sequence capable of hybridizing, under stringent conditions, to at least a portion of *D. immitis* nucleic acid sequence p22U; (e) an isolated parasitic helminth nucleic acid sequence capable of hybridizing, under stringent conditions, to at least a portion of *D. immitis* nucleic acid sequence p4; and/or (f) an isolated parasitic helminth nucleic acid sequence capable of hybridizing, under stringent conditions, to at least a portion of *D. immitis* nucleic acid sequence p22U.

Administration of a therapeutic composition containing multiple protective compounds targeting multiple parasitic helminths to an animal can protect the animal from infection by those helminths. Similarly, administration of a therapeutic composition targeting different aspects of a given parasitic helminth may provide additional protection to the animal. For example, a therapeutic composition of the present invention can include at least one of the following additional compounds: *D. immitis* P39, *D. immitis* P22L, *D. immitis* P20.5, *D. immitis* Di22, and *D. immitis* proteases expressed in L3 and/or L4 larvae, as well as other helminth proteins sharing significant homology with *D. immitis* P39, *D. immitis* P22L, *D. immitis* P20.5, *D. immitis* Di22, and *D. immitis* proteases expressed in L3 and/or L4 larvae, as well as mimetopes of such proteins, antibodies that selectively bind to such proteins or mimetopes thereof, and nucleic acid sequences encoding such proteins.

As used herein, a protective compound refers to a compound that when administered to an animal in an effective manner is able to treat, ameliorate, and/or prevent infection by a parasitic helminth. Preferred helminths are heretofore disclosed.

Therapeutic compositions of the present invention can be administered to any animal, preferably to mammals, and more preferably to dogs, cats, humans, ferrets, horses, cattle, sheep and other pets and/or economic food animals. Preferred animals to protect include dogs, cats, humans and ferrets, with dogs and cats being particularly preferred.

Therapeutic compositions of the present invention can be formulated in an excipient that the animal to be treated can tolerate. Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m or o-cresol, formalin and benzyl alcohol. Standard formulations will either be liquid injectables or solids which can be taken up in a suitable liquid as a suspension or solution for injection. Thus, in a non-liquid formulation, the excipient may comprise dextrose, human serum albumin, preservatives, etc., to which sterile water or saline could be added prior to administration.

In one embodiment of the present invention, the therapeutic composition can also include an immunopotentiator, such as an adjuvant or a carrier. Adjuvants are typically substances that generally enhance the immune response of an animal to a specific antigen. Suitable adjuvants include, but are not limited to, Freund's adjuvant; other bacterial cell wall components; aluminum-based salts; calcium-based salts; silica; polynucleotides; toxoids; serum proteins; viral coat proteins; other bacterial-derived preparations; gamma interferon; block copolymer adjuvants, such as Hunter's Titermax adjuvant (Vaxcel™, Inc. Norcross, Ga.); Ribi adjuvants (available from Ribi ImmunoChem Research, Inc., Hamilton, Mont.); and saponins and their derivatives, such as Quil A (available from Superfos Biosector A/S, Denmark). Carriers are typically compounds that increase the half-life of a therapeutic composition in the treated animal. Suitable carriers include, but are not limited to, polymeric controlled release formulations, biodegradable implants, liposomes, bacteria, other viruses, oils, esters, and glycols.

In order to protect an animal from parasitic helminth infection, a therapeutic composition of the present invention is administered to the animal in an effective manner such that the composition is capable of protecting that animal from infection. For example, an isolated protein or mimetope thereof, when administered to an animal in an effective manner, is able to elicit (i.e., stimulate) an immune response, preferably including both a humoral and cellular response, that is sufficient to protect the animal from infection. Similarly, an antibody of the present invention, when administered to an animal in an effective manner, is administered in an amount so as to be present in the animal at a titer that is sufficient to protect the animal from infection, at least temporarily. Nucleic acid sequences of the present invention, preferably oligonucleotides, can also be administered in an effective manner, thereby reducing expression of parasitic helminth proteins in order to interfere with parasite development.

Therapeutic compositions of the present invention can be administered to animals prior to parasite infection in order to prevent infection and/or can be administered to animals after parasite infection in order to treat disease caused by the parasite. For example, proteins, mimetopes thereof, and antibodies thereof can be used as immunotherapeutic agents.

Acceptable protocols to administer therapeutic compositions in an effective manner include individual dose size, number of doses, frequency of dose administration, and mode of administration. Determination of such protocols can be accomplished by those skilled in the art. A suitable single dose is a dose that is capable of protecting an animal from parasitic helminth infection when administered one or more times over a suitable time period. For example, a preferred single dose of a protein, mimetope or antibody therapeutic composition is from about 1 microgram ($\mu$g) to about 10 milligrams (mg) of the therapeutic composition for an animal about the size of a dog. Booster vaccinations can be administered from about 2 weeks to several years after the original administration. Preferably booster vaccinations are administered when the immune response of the animal becomes insufficient to protect the animal from parasitic helminth infection. A referred administration schedule is one in which from about 10 $\mu$g to about 1 mg of the vaccine per kg body weight of the animal is administered from about one to about two times over a time period of from about 2 weeks to about 12 months. Modes of administration can include, but are not limited to, subcutaneous, intradermal, intravenous, nasal, oral, transdermal and intramuscular routes.

According to one embodiment, nucleic acid sequences of the present invention can also be administered to an animal in a fashion to enable expression of the nucleic acid sequence into a protective protein in the animal to be protected from parasitic helminth infection. Nucleic acid sequences can be delivered in a variety of methods including, but not limited to, direct injection (e.g., as "naked" DNA or RNA molecules, such as is taught, for example in Wolff et al., 1990, *Science* 247, 1465–1468), packaged as a recombinant virus particle vaccine, and packaged as a recombinant cell vaccine.

A recombinant virus particle vaccine of the present invention includes a recombinant molecule of the present invention that is packaged in a viral coat and that can be expressed in an animal after administration. Preferably, the recombinant molecule is packaging-deficient. A number of recombinant virus particles can be used, including, but not limited to, those based on alphaviruses, pox viruses, adenoviruses, herpes viruses, and retroviruses. Preferred recombinant particle viruses are those based on alphaviruses, with those based on Sindbis virus, Semliki virus, and Ross River virus being more preferred. Methods to produce and use recombinant virus particle vaccines are disclosed in U.S. patent application Ser. No. 08/015,414, filed Feb. 8, 1993, entitled "Recombinant Virus Particle Vaccines", which is incorporated by reference herein in its entirety.

When administered to an animal, the recombinant virus particle vaccine infects cells within the immunized animal and directs the production of a parasitic helminth protein or RNA that is capable of protecting the animal from infection by the helminth. For example, when the helminth protein is a *D. immitis* protein, the recombinant virus particle vaccine is administered according to a protocol that results in the animal producing a sufficient immune response to protect itself from heartworm. A preferred single dose of a recombinant virus.particle vaccine of the present invention is from about $1 \times 10^4$ to about $1 \times 10^5$ virus plaque forming units (pfu) per kilogram body weight of the animal. Administration protocols are similar to those described herein for protein-based vaccines.

A recombinant cell vaccine of the present invention includes recombinant cells of the present invention that express at least one parasitic helminth protein. Preferred recombinant cells include Salmonella, *Escherichia coli*, and Mycobacterium recombinant cells, with Salmonella recombinant cells being more preferred. Such recombinant cells can be administered in a variety of ways but have the advantage that they can be administered orally, preferably at doses ranging from about $10^8$ to about $10^{12}$ bacteria per kilogram body weight. Administration protocols are similar to those described herein for protein-based vaccines. In common with most other enteric pathogens, Salmonella strains normally enter the host orally. Once in the intestine, they interact with the mucosal surface, normally to establish an invasive infection. Most Salmonella infections are controlled at the epithelial surface, causing the typical Salmonella-induced gastroenteritis. Some strains of Salmonella, including *S. typhi* and some *S. typhimurium* isolates, have evolved the ability to penetrate deeper into the host, causing a disseminated systemic infection. It appears such strains have the capacity to resist the killing actions of macrophages and other immune cells. *S. typhi* can exist for long periods as a facultative intracellular parasite. Some of the live vaccine strains can also persist for long periods in the mononuclear phagocyte system. Hosts infected in such a manner develop, in addition to a mucosal immune response, systemic cellular and serum antibody responses to the Salmonella. Thus, invading Salmonella, whether virulent or attenuated, can stimulate strong immune responses, unlike many other enteric pathogens which only set up local, noninvasive gut infections. The potent immunogenicity of live Salmonella makes them attractive candidates for carrying parasitic helminth proteins to the immune system.

A preferred recombinant cell-based vaccine is one in which the cell is attenuated. *Salmonella typhimurium* strains, for example, can be attenuated by introducing mutations into genes critical for in vivo growth and survival. For example, genes encoding cyclic adenosine monophosphate (cAMP) receptor protein or adenylate cyclase are deleted to produce avirulent, vaccine strains. Such strains can deliver antigens to lymphoid tissue in the gut but demonstrate reduced capacity to invade the spleen and mesenteric lymph nodes. These strains will still stimulate both humoral and cellular immunity in mammalian hosts.

Recombinant cell vaccines can be used to introduce isolated proteins of the present invention into the immune systems of animals. For example, recombinant molecules comprising parasitic helminth nucleic acid sequences of the present invention operatively linked to expression vectors that function in Salmonella can be transformed into Salmonella host cells. The resultant recombinant cells are then introduced into the animal to be protected. Preferred Salmonella host cells are those for which survival depends on their ability to maintain the recombinant molecule (i.e., a balanced-lethal host-vector system). An example of such a preferred host/recombinant molecule combination is a Salmonella strain (e.g., UK-1 $_\chi$3987 or SR-11 $_\chi$4072) which is unable to produce aspartate β-semialdehyde dehydrogenase in combination with a recombinant molecule also capable of encoding the enzyme. Aspartate β-semialdehyde dehydrogenase, encoded by the asd gene, is an important enzyme in the pathway to produce diaminopimelic acid (DAP). DAP is an essential component of the peptidoglycan of the cell wall of Gram-negative bacteria, such as Salmonella, and, as such, is necessary for survival of the cell. Thus, Salmonella lacking a functional asd gene can only survive if they maintain a recombinant molecule that is also capable of expressing a functional asd gene.

The efficacy of a therapeutic composition of the present invention to protect an animal from infection by a parasitic helminth can be tested in a variety of ways including, but not limited to, detection of protective antibodies (using, for example, proteins or mimetopes of the present invention), detection of cellular immunity within the treated animal, or challenge of the treated animal with the parasitic helminth or antigens thereof to determine whether the treated animal is resistant to infection. Such techniques are known to those skilled in the art.

One preferred embodiment of the present invention is the use of *D. immitis* nucleic acids and proteins to protect an animal from heartworm infection. It is particularly preferred to prevent L3 larvae that are delivered to the animal by the mosquito intermediate host from maturing into adult worms. As such, preferred therapeutic compositions are those that are able to inhibit at least one step in the portion of the parasite's development cycle that includes L3 larvae, third molt, L4 larvae, fourth molt, immature adult prior to entering the circulatory system. In dogs, his portion of the development cycle is about 70 days. As such, preferred nucleic acid sequences, proteins, and antibodies to protect an animal against heartworm include *D. immitis* p4 and *D. immitis* p22U, as well as nucleic acid sequences including at least a portion of *D. immitis* p4 and/or *D. immitis* p22U, proteins encoded by those sequences, mimetopes of such proteins, and antibodies that selectively bind to such proteins. Particularly preferred therapeutic compositions include proteins that share at least some *D. immitis* P4 and/or *D. immitis* P22U epitopes. Such compositions are administered to animals in a manner effective to protect the animals from heartworm infection. Additional protection may be obtained by administering additional protective compounds, including other *D. immitis* antigens, such as *D. immitis* P39, *D. immitis* P22L, *D. immitis* P20.5, *D. immitis* Di22, and/or *D. immitis* proteases expressed in L3 and/or L4 larvae.

It is also within the scope of the present invention to use the isolated parasitic helminth proteins, mimetopes, nucleic acid sequences, and antibodies as diagnostic agents. Preferably such diagnostic agents are supplemented with additional compounds that can detect other phases of the helminth's life cycle.

One embodiment of the present invention is a therapeutic composition capable of protecting an animal from parasitic helminth infection when administered to the animal in an effective manner that includes a compound capable of substantially interfering with the function of a parasitic helminth protein LDLr class A cysteine-rich motif, preferably by reducing the ability of such a protein to take up sterols. As used herein, a parasitic helminth protein LDLr class A cysteine-rich motif, or LDLr class A motif, refers to cysteine-rich motifs in parasitic helminth proteins that are homologous to that identified in *D. immitis* P4. Such motifs also occur in several other proteins, including LDL receptor-related proteins and $\alpha_2$-macroglobulin receptors, as heretofore disclosed. As used herein, substantially interferes refers to the ability of the compound to inhibit parasitic helminth development.

Preferred therapeutic compositions are those that are targeted to the LDLr class A motif shared by *D. immitis* P4 and other parasitic helminth proteins encoded, at least in part, by a nucleic acid sequence capable of hybridizing, under stringent conditions, to at least a portion of *D. immitis* p4. Suitable compounds can be identified by a variety of methods, including known methods to screen inorganic and organic molecules and rational drug design methods in which the active site of the motif is identified and a compound designed that would interfere with that active site. Suitable compounds are likely to include sterol mimetopes that are capable of interfering with sterol uptake by parasitic helminths, possibly by selectively binding to the LDLr class A motif.

Parasitic helminths, some protozoans and some insects are not able to synthesize squalenes and sterols de novo. Thus, parasitic helminths require sterols as precursors for steroid hormones and as integral structural components of cellular membranes. Cholesterol, one of the sterols that parasitic helminths cannot produce de novo, regulates cellular function, growth and differentiation by interacting with a number of protein kinases, protein receptors and ion pumps. Cholesterol is also the precursor of ecdysteroids, the steroidal molting hormones of insects, also believed to serve a similar function in parasitic helminths. While not being bound by theory, it is believed that the LDLr class A motif is important in the development of parasitic helminths (including nematodes, trematodes, and cestodes) as well as other organisms that do not synthesize sterols de novo (e.g., some parasitic protozoans and insects), because known LDLr class A motifs are apparently involved in sterol uptake. Such motifs in LDL receptors, for example, are responsible for binding the positively-charged ligands apolipoprotein B (apo B) and apolipoprotein E (apo E) within lipoprotein particles (see, for example, Herz et al., 1988, *EMBO J.* 7, p. 4119–4127). Apo E is involved in the clearance of triglyceride-rich lipoproteins and in reverse cholesterol transport. Apo E is also thought to be involved in the modulation of cell growth in mammalian lymphocytes as well as in brain and other tissues. Thus, compounds having the ability to interfere with sterol uptake by parasitic helminths due to their ability to interact with LDLr class A motifs are attractive as therapeutic compositions of the present invention.

Such therapeutic compositions can be administered to animals in an effective manner to protect animals from parasitic helminth infection. Effective amounts and dosing regimens can be determined using techniques known to those skilled in the art.

The following examples are provided for the purposes of illustration and are not intended to limit the scope of the invention.

EXAMPLES

Example 1

This Example describes a procedure for producing and evaluating immune sera of the present invention.

Four dogs were immunized with chemically-abbreviated *D. immitis* larval infections (using the method described in Grieve et al., 1988, ibid.), and two dogs served as chemically-treated controls. The dogs were housed in indoor mosquito-free individual cages at a temperature of about 22° C. and about 40% to about 65% humidity. On day 532, post initial immunization, each dog was challenged with about 100 L3 *D. immitis* larvae by implanting 5 diffusion chambers per dog, each diffusion chamber containing about 20 L3 *D. immitis* larvae, using the method described in Grieve et al., 1988, ibid. Concomitant with chamber implantation, each dog was injected subcutaneously with about 50 L3 *D. immitis* larvae, and the infection was allowed to proceed beyond the anticipated prepatent period. Challenge infections were repeated on day 588, post initial immunization, both by implanting 5 diffusion chambers per dog, each chamber having about 20 L3 *D. immitis* larvae and by subcutaneously inoculating about 30 L3 *D. immitis* larvae per dog. Serum samples were collected from the immunized dogs at numerous time points throughout the study period. Serum samples were analyzed for antibodies that selectively bound to L3 and/or L4 surface antigens using an indirect fluorescent antibody assay, and for antibodies that selectively bound to L3 soluble antigens, L4 soluble antigens and/or to an excretory/secretory antigen fraction using an indirect ELISA, as described by Grieve et al., 1988, ibid. The results indicated that serum from dogs that had been immunized and challenged with *D. immitis* larvae had produced antibodies to both surface and soluble *D. immitis* larval antigens. The sera were pooled, and those obtained from larval-immunized dogs (i.e., anti-larval immune sera) were shown to inhibit larval development; see, for example, Example 2. Immune sera were also shown to selectively bind to L3 and/or L4 larval proteins having molecular weights of about 15 kD, 23/24 kD doublet, 31 kD, 33 kD, 39 kD, 42 kD, 55 kD, 59 kD, 66 kD, 70 kD, 97 kD and 207 kD by Tris-glycine SDS PAGE.

Example 2

This Example demonstrates that serum collected from larval-immunized dogs, produced as described in Example 1, is capable of inhibiting parasite development whereas serum collected from non-immunized dogs is not.

One subcutaneous pocket was formed in each of about 3 to about 6 Balb/C BYJ mice that were about 10 weeks old. One diffusion chamber, containing 20 L3 *D. immitis* larvae, was implanted into each pocket alone with 0.5 ml of sera collected from immunized dogs or from non-immunized dogs, produced as described in Example 1. The diffusion chambers were recovered two or three weeks later. Living larvae in the chambers were counted and placed into glacial acetic acid, followed by 70% ethanol containing 5% glycerin. The ethanol was allowed to evaporate leaving the larvae in glycerin. The larvae were measured using projected images in the Macmeasure image analysis system on a Macintosh computer.

Three experiments, in which different serum samples were exposed to larvae in diffusion chambers, were conducted: Experiment 1 compared equal portions of sera collected from individual dogs at days 56, 77 and 117 after challenge. Experiments 2 and 3 compared serum collected from immunized dogs 117 days after initial challenge to control sera. In experiment 2, the control serum was a pool of sera collected from 12 naive dogs; in experiment 3, control serum was collected from a single naive dog. Each of the experiments also included controls in which the larvae were not exposed to any serum.

In experiment 1, chambers were recovered two weeks post-inoculation. The number of larvae retrieved from chambers implanted in mice receiving serum from immunized (i.e., immune) dogs was lower than that of larvae in chambers implanted in mice receiving naive dog serum, but the difference was not statistically significant. Also, no differences were seen between the length of larvae regardless of which serum was used.

In experiments 2 and 3, the chambers were recovered three weeks after infection. There were significant differences in the larval recoveries between those receiving serum from naive dogs and those from immune dogs; there were about 34% more larvae recovered from mice treated with naive dog serum than were recovered from mice treated with immune serum. The lengths of the larvae were also significantly shorter in those chambers exposed to sera from immune dogs compared to larvae in chambers exposed to naive dog sera. Thus, this Example shows that serum collected from dogs immune to *D. immitis* infection inhibits larval development, compared to serum collected from naive dogs.

Example 3

This Example describes the purification of *D. immitis* P22U as well as tryptic digestion of the protein, and partial amino acid sequencing of several tryptic fragments.

Third stage larvae were collected and cultured in vitro as described in Frank et al., 1992, ibid. The larvae were washed free of serum proteins at about 48 hr, placed back into culture and the serum-free media containing larval ES products was collected from 48 to 144 hr in culture. Each week's yield of ES was collected, filtered through a 0.45 μm filter (Acrodiscm, Gelman Sciences, Ann Arbor, Mich.) and frozen at about −70° C. until further processing. Processing was conducted at about 4° C. or on ice and consisted of thawing the ES and adding 0.5 M EDTA.Na$_2$, pH 8.0, to a final concentration of 5 mM. EDTA was the only protease inhibitor used since only metalloprotease activity has been found in larval ES (Richer et al., 1992, *Exp. Parasit.* 75, p. 213–222). The ES was concentrated and the buffer was exchanged using Centriprep-10 and Centricon-10 (Amicon, Beverly, Mass.); the final buffer was 20 mM Tris, 1 mM EDTA.Na$_2$, pH 7.2.

All chromatography was performed on a Beckman 338 binary system using System Gold version 3.10 chromatography software (Beckman Instruments, Inc., San Ramon, Calif.). The separations and fraction collections were conducted at room temperature and the fractions placed at about 4° C. immediately after each run. When portions of the samples were metabolically labeled, aliquots of the collected fractions were assayed in scintillation fluid by a Beckman Model LS 1801 liquid scintillation counter (Beckman Instruments, Inc.).

The first purification was from approximately 38,650 larvae, 3,550 of which had been metabolically labeled with Translabel™ from about 48 to 144 hr. The ES products were concentrated to 175 μl in 20 mM Tris, 1 mM EDTA.Na$_2$, pH 7.2 (Buffer A) and contained 1.3 μg/μl protein with an $^{35}$S-incorporation of 7,450 cpm/μl. Cation exchange chromatography was used as the first step in purification. A SynChropak CM300-GRD 4.6×50 mm column (Synchrom, Inc., Lafayette, Ind.) was used. The sample was diluted with 300 μl buffer A, centrifuged at 12,000 g and the supernate injected onto the column at 0.5 ml/min Buffer A. After a 5 min wash, the adsorbed proteins were eluted with a steep gradient to 100% Buffer B (1 M KCl in Buffer A) over 0.1 min while 200 μl fractions were collected throughout. Detection of proteins was at 280 nm. FIG. 1 shows the resultant chromatogram. Boxed fractions, designated 4, 5, 6, 23, 24, 25 and 26, were evaluated by SDS PAGE.

The vast majority of contaminating proteins eluted in the initial peak. In contrast, P22U, as well as P22L and P20.5, eluted in the second peak, i.e., in fractions 23, 20 24, 25 and 26.

Reverse phase chromatography using a Vydac C$_4$ 0.21×25 cm, 5 μm particle size column (Vydac 214TP52, The Separations Group, Hesperia, Calif.) was used to separate P22U from P22L and P20.5. Buffer C consisted of 0.1% trifluoroacetic acid (TFA), 0.085% triethylamine (TEA) in Milli-Q water produced by processing 18 megaohm water through a Milli-Q Plus water system (Millipore Corp., Bedford Mass.), while Buffer D consisted of 0.085% TFA, 0.085% TEA, 80% CH$_3$CN in Milli-Q water. Detection of proteins was at 220 nm. Fractions 23 and 24 from the cation exchange run were injected onto the column followed by fractions 25 and 26 two min later. The initial flow rate was 0.25 ml/min at 12.5% D, 87.5% C. The flow rate was reduced to 0.17 ml/min at 4 min and a gradient to 62.5t D over 200 min was started at 6 min. Fractions of 0.75 min were collected.

Aliquots of peak fractions were submitted to SDS-PAGE and analyzed by silver staining and autoradiography. P20.5 appeared first and predominated in fractions 99–102 (elution times of from about 74.25 minutes through about 76.5 minutes). P22L predominated in fractions 103–107 (elution times of from about 77.25 minutes through about 80.25 minutes), although there was significant contamination with P20.5. P22U eluted much later, in fractions 229–235 (elution times of from about 171.75 minutes through about 176.25 minutes).

Purified P22U obtained from C$_4$ reverse phase chromatography was denatured, reduced and pyridylethylated by standard procedures (see, for example, Matsudaira, P. T. (ed.)., 1989, *A Practical Guide to Protein and Peptide Purification for Microseguencing*). The pyridylethylated P22U was subjected to trypsin digestion, and the tryptic peptides separated by C$_{18}$ reverse phase chromatography using a 0.21-cm×25-cm, 5-μm particle size column (Vydac 218TP52) by a procedure based on Stone et al., 1989, in Matsudaira, P. T. (ed.)., *A Practical Guide to Protein and Purification for Microsequencing*, p. 31–47.

Figure 2:
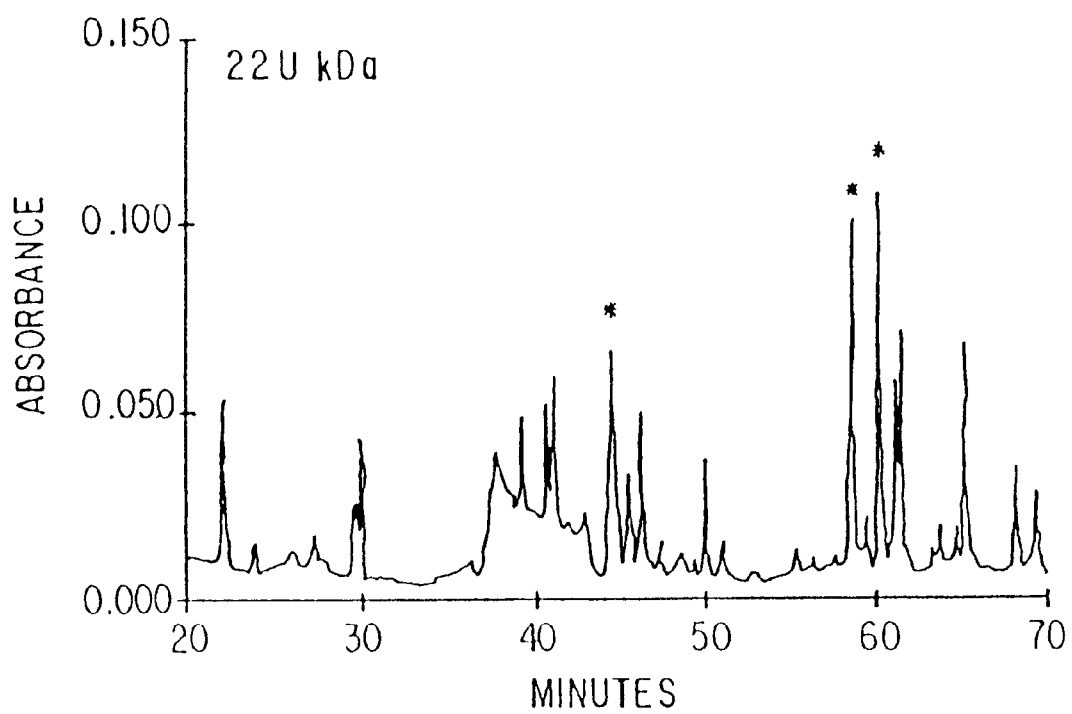
FIG. 2 depicts a chromatogram of the separation of tryptic fragments of P22U by $c_{18}$ reverse phase chromatography; P22U was purified by cation exchange and $C_4$ reverse phase chromatography.

The chromatogram depicting the tryptic fragments of P22U is shown in FIG. 2. The fragments indicated by asterisks were submitted for sequencing. All sequencing was conducted at Macromolecular Resources, Department of Biochemistry, Colorado State University, Fort Collins, Colo. The peptides were concentrated to 50 μl or less using a Speedvac® and frozen at about −20° C. until sequencing. N-terminal sequencing was conducted in an ABI Model 473A Protein/Peptide Sequencer System (Applied Biosystems, Inc., Foster City, Calif.) using pulsed liquid chemistry and on line microgradient PTH amino acid analysis (see, for example, Hewick et. al., 1981, *J. Biol. Chem.* 256, p. 7990–7997; Geisow and Aitken, 1989, in Findlay, J. B. C. and M. J. Geisow (ed.). *Protein Sequencing: A Practical Approach*, p. 85–98). The most likely sequence of the tryptic fragment eluting at 44 minutes (referred to as the 44 min tryptic fragment), using one-letter amino acid code, was MAQDAFPNACAQGEPK, set forth in SEQ ID NO:6. The most likely sequence of the tryptic fragment eluting at 58 minutes (referred to as the 58 min tryptic fragment) was AIAPCQLTAVQSVLPCADQCQK, set forth in SEQ ID NO:7. The most likely sequence of the tryptic fragment eluting at 60 minutes (referred to as the 60 min tryptic fragment) was LGSCSPDCGLDLPSDNVMVQDV, set forth in SEQ ID NO:8.

Example 4

This Example describes the cloning and sequencing of *D. immitis* nucleic acid sequence p4. *D. immitis* p4 was identified by its ability to encode a protein that electively bound to at least one component of immune serum collected from a dog immunized with *D. immitis* larvae.

*D. immitis* L3 larvae were harvested from mosquitos using standard techniques and cultivated in vitro in 50:50 NCTC-135/IMDM (NI) media (Sigma) supplemented with 20% serum supplement at 37° C., 5% carbon dioxide for 48 hours. Total RNA was extracted from the larvae using an acid-guanidinium-phenol-chloroform method similar to that described by Chomczynski and Sacchi, 1987, *Anal. Biochem.* 162, p. 156–159. Approximately 15,000 to 30,000 larvae were used in an RNA preparation. Poly A+ selected RNA was separated from total RNA by oligo-dT cellulose chromatography using Oligo dT cellulose from Collaborative Research, Inc., Waltham, Mass., according to the method recommended by the manufacturer.

A *D. immitis* L3 larval cDNA expression library was constructed in lambda (λ) Uni-ZAP™ XR vector (available from Stratagene Cloning Systems, La Jolla, Calif.) using Stratagene's ZAP-cDNA Synthesis Kit® protocol and about 5 μg to about 6 μg of L3 poly A+. The resultant library was amplified to a titer of about $4.88 \times 10^9$ pfu/ml with about 97% recombinants.

Using the protocol described in the Stratagene picoBlue immunoscreening kit, the L3 larval cDNA expression library was screened with immune dog serum prepared as described in Example 1. Antibodies specific for a highly immunoreactive protein termed the "ladder protein" (Culpepper et al., 1992, *Mol. Biochem. Parasitol.* 54, p. 51–62) had been adsorbed from this serum by affinity chromatography with a recombinant GST-ladder fusion protein. Immunoscreening of duplicate plaque lifts of the cDNA library with the same serum identified 4 positive clones, one of which included *D. immitis* nucleic acid sequence p4. The remaining 3 clones were shown to encode at least portions of P39, as disclosed in U.S. patent application Ser. No. 08/003,389, referenced above.

The plaque-purified clone including *D. immitis* nucleic acid sequence p4 was converted into a double stranded recombinant molecule, herein denoted as pβgal-p4, using R408 helper phage and XL1-Blue *E. coli* according to the in vivo excision protocol described in the Stratagene ZAP-cDNA Synthesis Kit. Double stranded plasmid DNA was prepared using an alkaline lysis protocol, such as that described in Sambrook et al., ibid. The plasmid DNA was digested with EcoRI and XhoI restriction endonucleases to release two *D. immitis* DNA fragments of about 580 and 320 nucleotides, the entire *D. immitis* p4 fragment being about 900 nucleotides in size.

The plasmid containing *D. immitis* p4 was sequenced using the Sanger dideoxy chain termination method, as described in Sambrook et al., ibid. The Promega Erase a Base method (available from Promega Corp., Madison, Wis.) was used to generate deletion clones for sequence analysis. An about 913-nucleotide consensus sequence of the entire *D. immitis* p4 DNA fragment was determined and is presented as SEQ ID NO:1. The entire 913 nucleotides form an open reading frame encoding an amino acid sequence of about 303 amino acids, presented in SEQ ID NO:2. The first ATG codon within this sequence spans nucleotides from about 417 through about 419. As such, SEQ ID NO:1 does not encode a full-length protein, but does encode a protein that selectively binds to at least one component of immune dog serum. The predicted size of the protein encoded by SEQ ID NO:1 is about 35.5 kD, with an estimated pI of about 4.26.

A homology search of the non-redundant protein sequence database was performed through the National Center for Biotechnology Information using the BLAST network. This database includes SwissProt+PIR+SPUpdate+GenPept+GPUpdate. The search was performed using SEQ ID NO:2 and showed the only significant homology shared between SEQ ID NO:2 and known sequences to be a contiguous stretch of 9 amino acids, namely DDCGDGSDE, set forth in SEQ ID NO:5, that was also found in human LDL-receptor related protein, human and mouse alpha-2-macroglobulin receptors and rat renal GP 330 glycoprotein. A conserved stretch of eight of the nine amino acids is also found in *Caenorhabditis elegans* LDL receptor-related protein and *C. elegans* basement membrane proteoglycan.

Example 5

This example demonstrates the ability of *D. immitis* p4 to encode a protein that selectively binds to immune serum.

Recombinant molecule pET19b-p4$_{635}$, containing *D. immitis* p4 nucleotides from about 1 through about 635 operatively linked to bacteriophage T7lac transcription control sequences and to a fusion sequence encoding a polyhistidine segment comprising 10 histidines was produced in the following manner. An about 635-nucleotide DNA fragment containing nucleotides spanning from about 1 through about 635 of SEQ ID NO:1, called P4$_{635}$, was PCR amplified from a clone containing *D. immitis* p4 using the primers 5' CGGGATCCCGAGTTAAATAGTCG 3' (denoted SEQ ID NO:9 or 394-5'; BamHI site underlined) and 5' TGCAGGATCCTGCACCG 3' (denoted SEQ ID NO:10 or 394-3'; BamHI site underlined). The PCR product was digested with BamHI restriction endonuclease, gel purified and subcloned into expression vector pET19b (available from Novagen Inc., Madison, Wis.) that had been cleaved with BamHI. The resulting recombinant molecule pET19b-p4$_{635}$ was transformed into *E. coli* BL21(DE3)pLysS to form recombinant cell *E. coli*:pET19b-p4$_{635}$. *E. coli* BL21(DE3)pLysS includes a bacteriophage T7 RNA polymerase gene under the control of lac transcription control sequences.

Recombinant cell *E. coli*:pET19b-p4$_{635}$ was cultured in shake flasks containing an enriched bacterial growth medium containing 0.1 mg/ml ampicillin at about 37° C. When the cells reached an optical density at about 600 nanometers (OD$_{600}$) of about 0.819, expression of *D. immitis* p4 was induced by addition of about 1 mM isopropyl-β-D-thiogalactoside (IPTG). Protein production was monitored by SDS PAGE of recombinant cell lysates, followed by Coomassie blue staining, using standard techniques. Recombinant cell *E. coli*:pET19b-p4$_{635}$ produced a protein, denoted PHIS-P4$_{635}$, that migrated with an apparent molecular weight of about 37 kD. Such a protein was not produced by cells transformed with the pET-19b plasmid lacking a *D. immitis* DNA insert.

Immunoblot analysis of recombinant cell *E. oli*:pET19b-p4$_{635}$ lysates indicates that the 37 kD protein is able to selectively bind to immune dog serum and, as such, is capable of binding to at least one component of a serum that is capable of inhibiting *D. immitis* larval development.

The *E. coli*:pET19b-p4$_{635}$ histidine fusion peptide was separated from soluble *E. coli* proteins by nickel chelation chromatography and an imidazole gradient. Immunoblot analysis of the total *E. coli*:pET19b-p4$_{635}$ lysate, column eluate and column void volume indicates that the 37 kD protein can be isolated on the nickel column and is able to selectively bind to immune dog serum and, as such, is capable of binding to at least one component of a serum that is capable of inhibiting *D. immitis* larval development. The column eluate was not detected by preimmune sera from the same immune dog.

Example 6

This Example describes the isolation and sequence of *D. immitis* nucleic acid sequence p22U.

Total RNA was extracted from adult female *D. immitis* worms, poly A+ RNA prepared, and an adult female *D.*

*immitis* cDNA library produced, using methods similar to those described in Example 4.

A segment of DNA for use in the identification of a nucleic acid sequence capable of encoding at least a portion of P22U was produced by PCR amplification using standard techniques, such as those described in Sambrook et al., ibid. Briefly, first strand cDNA was synthesized from adult female poly A+ RNA using Murine Leukemia Virus reverse transcriptase (available from Stratagene) and Stratagene's linker-primer from their ZAP-cDNA Synthesis Kit, namely 5' GAGAGAGAGAGAGAGAGAAC-TAGTCTCGAGTTTTTTTTTTTTTTTTTT 3', set forth in SEQ ID NO:11. A pool of two sets of degenerate primers was produced based on the partial amino acid sequence of the 60 min tryptic fragment described in Example 3. One degenerate set of primers, denoted GRF 11, includes the following sequences: 5' TGYTCNCCNGAYTGYGG 3', set forth in SEQ ID NO:12, wherein Y can be either C or T, and N can be either A, G, C or T. The second set of primers, denoted GRF 12, includes the following sequences: 5' TGYAGTCCNGAYTGYGG 3', set forth in SEQ ID NO:13. PCR amplification using the pool of degenerate primers in combination with Stratagene's linker-primer as the antisense primer was used to amplify the DNA segment. Verification that the appropriate segment had been amplified was accomplished by Southern blot analysis using a degenerate probe based on a more C-terminal amino acid sequence of the 60 min tryptic fragment, namely GRF 3 which includes the following sequences: 5' TGNACCATNACRTTRTC 3', set forth in SEQ ID NO:14, wherein R can be either A or G.

The amplified segment was gel purified, electroeluted and cloned into the pCR II cloning vector (available from Invitrogen, San Diego, Calif.), following the manufacturers' instructions. Two clones were partially sequenced, yielding a nucleic acid sequence which included a sequence corresponding to the amino acid sequence of the 60 min tryptic fragment. The nucleic acid sequence includes from nucleotides about 444 to about 696 of SEQ ID NO:3, described in more detail below.

The adult female cDNA library was screened with an antisense probe, using stringent (i.e., standard) hybridization conditions as described in Sambrook et al., ibid. The antisense probe, denoted GRF14, was based on the DNA sequence derived from the amplified segment and has the sequence 5' CTGTTTGAACCATAACATTATCAGATGG 3', set forth in SEQ ID NO:15. Plaques which hybridized to the probe were rescreened, plaque purified and clones containing *D. immitis* nucleic acid sequence p22U (i.e., clones that hybridized with the antisense probe and having the apparent nucleic acid sequence designated in SEQ ID NO:3) were submitted to nucleic acid sequencing as described in Example 4.

An about 1016-nucleotide consensus sequence of *D. immitis* nucleic acid sequence p22U was determined and is presented as SEQ ID NO:3. The deduced translation product is presented both with SEQ ID NO:3 and in SEQ ID NO:4. SEQ ID NO:3 apparently encodes a protein of about 208 amino acids, the sequence including a stop codon spanning nucleotides about 627 through about 629. There are two ATG codons spanning nuclectides about 39 to about 41 and spanning nucleotides about 57 to about 59. Although SEQ ID NO:3 encodes a protein of about the expected size (i.e., edicted size of about 22 kD), the actual translation nitiation site of the protein is as yet unknown.

Nucleic acid sequences encoding all three partially sequenced tryptic peptides are included in SEQ ID NO:3, indicating that the sequence does encode at least a portion of P22U. The portion of the 44 min tryptic fragment that was sequenced spans amino acids about 77 to about 92 of SEQ ID NO:4 and agrees with the derived sequence in all but one amino acid. The portion of the 58 min tryptic fragment that was sequenced spans amino acids about 27 to about 48 of SEQ ID NO:4 and agrees with the derived sequence in all but one amino acid. The portion of the 60 min tryptic fragment that was sequenced spans amino acids about 145 to about 166 of SEQ ID NO:4 and agrees with the derived sequence in all but one amino acid. A homology search of the non-redundant protein sequence database was performed through the National Center for Biotechnology Information using the BLAST network. This database includes SwissProt+PIR+SPUpdate+GenPept+GPUpdate. The search was performed using SEQ ID NO:4 and no significant homology with known proteins was indicated.

Example 7

This example demonstrates the ability of *D. immitis* p22U to encode a protein that selectively binds to immune serum.

Recombinant molecule pHis-p22U$_{608}$, containing *D. immitis* p22U nucleotides from about 41 through about 649 operatively linked to trc transcription control sequences and to a fusion sequence encoding a poly-histidine segment comprising 6 histidines was produced in the following manner. An about 608-nucleotide DNA fragment containing nucleotides spanning from about 41 through about 649 of SEQ ID NO:3, called p22U$_{608}$, was PCR amplified from a clone containing *D. immitis* p22U using the primers 5' GTTGCAATATGGGATCCAATGAGCC 3' (denoted SEQ ID NO:16 or 22USEN; BamHI site underlined) and 5' CGCTAGTGCAGGATCCTCAATACTC 3' (denoted SEQ ID NO:17 or 22UANT; BamHI site underlined). The PCR product was digested with BamHI restriction endonuclease, gel purified and subcloned into expression vector pTrcHisB (available from Invitrogen) that had been cleaved with BamHI. The resulting recombinant molecule pHis-p22U$_{608}$ was transformed into *E. coli* to form recombinant cell *E. coli*:pHis-p22U$_{608}$. The recombinant cell was cultured in shake flasks containing an enriched bacterial growth medium containing 0.1 mg/ml ampicillin at about 37° C. When the cells reached an OD$_{600}$ of about 0.3, expression of *D. immitis* p22U$_{608}$ was induced by addition of about 1 mM IPTG. Protein production was monitored by SDS PAGE of recombinant cell lysates, followed by Coomassie blue staining, using standard techniques. Recombinant cell *E. coli*:pHis-p22U$_{608}$ produced a protein, denoted herein as PHIS-P22U$_{608}$, that migrated with an apparent molecular weight of about 27 kD. Such a protein was not produced by cells transformed with the pTrcHisB plasmid lacking a *D. immitis* DNA insert.

Immunoblot analysis of recombinant cell *E. coli*:pHis-p22U$_{608}$ lysates indicates that the 22-kD protein is able to selectively bind to immune dog serum and, as such, is capable of binding to at least one component of a serum that is capable of inhibiting *D. immitis* larval development. Immune dog serum essentially does not bind to lysates of cells transformed with only the pTrcHisB plasmid.

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 913 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 3..911

(xi) SEQUENCE DESCRIPTION: SEQ ID NO:1:

```
GC GAG TTA AAT AGT CGA ATT TCC GGA GTA CAC CGT AAT ACT GCA GGT           47
   Glu Leu Asn Ser Arg Ile Ser Gly Val His Arg Asn Thr Ala Gly
    1               5                  10                  15

GCT TTA CAA CGA TTT GCT CTA AAT GGT CAA AAT ACT CTT AAC GAA GGA           95
Ala Leu Gln Arg Phe Ala Leu Asn Gly Gln Asn Thr Leu Asn Glu Gly
                20                  25                  30

TCA AGT TAT GAG CCA AAC GGA CTA TTT GTA TTT TCA GCA ATA AAC GGT          143
Ser Ser Tyr Glu Pro Asn Gly Leu Phe Val Phe Ser Ala Ile Asn Gly
            35                  40                  45

AGC CAT ACT GAT AGC TTA TCT CAG TAT GGT GAA GGA ATA AAT GAA AAT          191
Ser His Thr Asp Ser Leu Ser Gln Tyr Gly Glu Gly Ile Asn Glu Asn
        50                  55                  60

TAT CAT TCT GGA ACT AAT TAT TAT GAT GAA GTA GAA TTA AGA GAT AAA          239
Tyr His Ser Gly Thr Asn Tyr Tyr Asp Glu Val Glu Leu Arg Asp Lys
65                  70                  75

ACA AAT CAG ACA TCG TAC ATT AAT GGA AAT GAT AAT GGA ATC AAT GGA          287
Thr Asn Gln Thr Ser Tyr Ile Asn Gly Asn Asp Asn Gly Ile Asn Gly
    80                  85                  90                  95

AAG GAT GAT GAA GAT CTG GAT GAA TGC TCT GAT CAA GAA TTC CGA TGT          335
Lys Asp Asp Glu Asp Leu Asp Glu Cys Ser Asp Gln Glu Phe Arg Cys
                100                 105                 110

CCA TAT CTA GCT AAA ACA CTT TGT GTT CAT TAT TTG AAA ATA TGC GAT          383
Pro Tyr Leu Ala Lys Thr Leu Cys Val His Tyr Leu Lys Ile Cys Asp
            115                 120                 125

GGT ATT GAT GAT TGT GGT GAT GGA AGT GAT GAA ATG AAC TGT GCT GAT          431
Gly Ile Asp Asp Cys Gly Asp Gly Ser Asp Glu Met Asn Cys Ala Asp
        130                 135                 140

GAT GAA GTG ATA ACA TCA ATA AAT GGT AAC GAA TCA ATC AAT ATC AGA          479
Asp Glu Val Ile Thr Ser Ile Asn Gly Asn Glu Ser Ile Asn Ile Arg
    145                 150                 155

TGT GAT CCG GAT CAA TTT CGA TGT GAA AAT GGA AAA TGT ATC GCA CAA          527
Cys Asp Pro Asp Gln Phe Arg Cys Glu Asn Gly Lys Cys Ile Ala Gln
160                 165                 170                 175

ATT GAT CGA TGT AAT CGA AAA TAT GAT TGT GAT GAT GGT ACA GAT GAA          575
Ile Asp Arg Cys Asn Arg Lys Tyr Asp Cys Asp Asp Gly Thr Asp Glu
                180                 185                 190

ACA ACT TGT GAA TAT TTC GTG CAA GCT TTG CAA CAA GCG AGA GGT GTA          623
Thr Thr Cys Glu Tyr Phe Val Gln Ala Leu Gln Gln Ala Arg Gly Val
            195                 200                 205

ACG GTG CAG GAT AAT GCA ATT CGA GAT GAC GAG ATA CCA AAT TAT ACT          671
Thr Val Gln Asp Asn Ala Ile Arg Asp Asp Glu Ile Pro Asn Tyr Thr
        210                 215                 220
```

```
GTA TCC ATG GAA CAG AAA TAC GAT CAA GTA AAG GAA GAT AAG GAG CGG                    719
Val Ser Met Glu Gln Lys Tyr Asp Gln Val Lys Glu Asp Lys Glu Arg
    225                 230                 235

CGA ATG CAA GAG GAG GAG GAA CAG GAA AGG CTG AGA GAG TAC GAG GAA                    767
Arg Met Gln Glu Glu Glu Glu Gln Glu Arg Leu Arg Glu Tyr Glu Glu
240                 245                 250                 255

CAG ATA CAG GAA AAA TTG AGG CAG GAG GAA GAA AGA GAA CGG CAA GAA                    815
Gln Ile Gln Glu Lys Leu Arg Gln Glu Glu Arg Glu Arg Gln Glu
                260                 265                 270

CAG GAA AGA AGA CAA AAG GAA CGA GAA AGA ATG GAA CAA GAA AGG ATA                    863
Gln Glu Arg Arg Gln Lys Glu Arg Arg Met Glu Gln Glu Arg Ile
            275                 280                 285

AGA CAA GAA TAT GAT GAA AAG GAA AGA CAA AGG CAA TAT GCT GAA CAG                    911
Arg Gln Glu Tyr Asp Glu Lys Glu Arg Gln Arg Gln Tyr Ala Glu Gln
        290                 295                 300

GC                                                                                 913
```

(2) INFORMATION FOR SEQ ID NO:2:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:2:

```
Glu Leu Asn Ser Arg Ile Ser Gly Val His Arg Asn Thr Ala Gly Ala
  1               5                  10                  15

Leu Gln Arg Phe Ala Leu Asn Gly Gln Asn Thr Leu Asn Glu Gly Ser
                20                  25                  30

Ser Tyr Glu Pro Asn Gly Leu Phe Val Phe Ser Ala Ile Asn Gly Ser
            35                  40                  45

His Thr Asp Ser Leu Ser Gln Tyr Gly Glu Gly Ile Asn Glu Asn Tyr
        50                  55                  60

His Ser Gly Thr Asn Tyr Tyr Asp Glu Val Glu Leu Arg Asp Lys Thr
 65                  70                  75                  80

Asn Gln Thr Ser Tyr Ile Asn Gly Asn Asp Asn Gly Ile Asn Gly Lys
                85                  90                  95

Asp Asp Glu Asp Leu Asp Glu Cys Ser Asp Gln Glu Phe Arg Cys Pro
            100                 105                 110

Tyr Leu Ala Lys Thr Leu Cys Val His Tyr Leu Lys Ile Cys Asp Gly
        115                 120                 125

Ile Asp Asp Cys Gly Asp Gly Ser Asp Glu Met Asn Cys Ala Asp Asp
    130                 135                 140

Glu Val Ile Thr Ser Ile Asn Gly Asn Glu Ser Ile Asn Ile Arg Cys
145                 150                 155                 160

Asp Pro Asp Gln Phe Arg Cys Glu Asn Gly Lys Cys Ile Ala Gln Ile
                165                 170                 175

Asp Arg Cys Asn Arg Lys Tyr Asp Cys Asp Asp Gly Thr Asp Glu Thr
            180                 185                 190

Thr Cys Glu Tyr Phe Val Gln Ala Leu Gln Gln Ala Arg Gly Val Thr
        195                 200                 205

Val Gln Asp Asn Ala Ile Arg Asp Asp Glu Ile Pro Asn Tyr Thr Val
    210                 215                 220

Ser Met Glu Gln Lys Tyr Asp Gln Val Lys Glu Asp Lys Glu Arg Arg
225                 230                 235                 240
```

```
Met Gln Glu Glu Glu Gln Glu Arg Leu Arg Glu Tyr Glu Glu Gln
                245                 250                 255

Ile Gln Glu Lys Leu Arg Gln Glu Glu Arg Glu Arg Gln Glu Gln
                260                 265                 270

Glu Arg Arg Gln Lys Glu Arg Glu Arg Met Glu Gln Glu Arg Ile Arg
                275                 280                 285

Gln Glu Tyr Asp Glu Lys Glu Arg Gln Arg Gln Tyr Ala Glu Gln
                290                 295                 300

(2) INFORMATION FOR SEQ ID NO:3:

(i) SEQUENCE CHARACTERISTICS:
        (A) LENGTH: 1016 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..626

(ix) FEATURE:
        (A) NAME/KEY: 3'UTR
        (B) LOCATION: 627..1016

(xi) SEQUENCE DESCRIPTION: SEQ ID NO:3:
```

```
GT TTT GTT GTA CTA CTC GTT GTT GCA ATA TGG ATT GAA ATG AGC CAA        47
   Phe Val Val Leu Leu Val Val Ala Ile Trp Ile Glu Met Ser Gln
   1               5                   10                  15

GGC CAA CAA ATG ATC AAA CAA TGT AAA TGT TCT GAT ATT GCA CCA TGT       95
Gly Gln Gln Met Ile Lys Gln Cys Lys Cys Ser Asp Ile Ala Pro Cys
                20                  25                  30

CAA TTA ACT GCC GTT CAA TCA GTT TTA CCA TGT GCT GAT CAA TGC CAG      143
Gln Leu Thr Ala Val Gln Ser Val Leu Pro Cys Ala Asp Gln Cys Gln
                35                  40                  45

AAA TAT ATT ACT TCA ATT GGT GGT AAT TAT GAT CAA ATT AGT AAC TGT      191
Lys Tyr Ile Thr Ser Ile Gly Gly Asn Tyr Asp Gln Ile Ser Asn Cys
                50                  55                  60

TTT AAA CAG AAA CAA TCA ATT ATA AAT GAT GCT ATG AAA TGT GCT CAA      239
Phe Lys Gln Lys Gln Ser Ile Ile Asn Asp Ala Met Lys Cys Ala Gln
65                  70                  75

GAT GCT TTC CCA AAT GCA TGC GCA CAA GGT GAA CCA AAA ATG GTA CCA      287
Asp Ala Phe Pro Asn Ala Cys Ala Gln Gly Glu Pro Lys Met Val Pro
80                  85                  90                  95

AAA CGA TTC GGA AAA GGT CTT CAA TTA GCT GTA ATG ACT GAT ATC AAC      335
Lys Arg Phe Gly Lys Gly Leu Gln Leu Ala Val Met Thr Asp Ile Asn
                100                 105                 110

AAA GAA TTA CAA CGA ATG GGA ATA GCA AAT CAA GTT ACT CAA CTA ATC      383
Lys Glu Leu Gln Arg Met Gly Ile Ala Asn Gln Val Thr Gln Leu Ile
                115                 120                 125

TCC CAA GGT CGA CGA TTC TTT AAA TGC TTC CAA TCG TGT ATG ATG AAA      431
Ser Gln Gly Arg Arg Phe Phe Lys Cys Phe Gln Ser Cys Met Met Lys
                130                 135                 140

AAA TTG GGC TCA TGT TCT CCA GAT TGT GGT CTT GAT TTA CCA TCT GAT      479
Lys Leu Gly Ser Cys Ser Pro Asp Cys Gly Leu Asp Leu Pro Ser Asp
145                 150                 155

AAT GTT ATG GTT CAA ACA GTT AAA AAT TGC GCT CAA AAA AGT GGT ATT      527
Asn Val Met Val Gln Thr Val Lys Asn Cys Ala Gln Lys Ser Gly Ile
160                 165                 170                 175

CAA ACT GCA TCG GTG CAA GAT CTT TGC TTT TGC GTC GAA CAA GCT GGT      575
```

```
Gln Thr Ala Ser Val Gln Asp Leu Cys Phe Cys Val Glu Gln Ala Gly
                180                 185                 190

ATT CGG CAA CTT TCT GAT GTA TGT CCT CGT ATA CAA ATT TTC AAA ACG      623
Ile Arg Gln Leu Ser Asp Val Cys Pro Arg Ile Gln Ile Phe Lys Thr
            195                 200                 205

AAA TGAGTATTGA GAATATTGCA CTAGCAGCAA TCATTATTTT TCTCGAGAAT           676
Lys

TTTCGCTATC AATAAGTTGG AATATGATTA CAATAATATA TATATTAACT GCAAAAATCT    736

TTCTTCTTCA AAATTATTTT TCATTTCGCT CTCATAATTG CATGATAATA GTCATAATGA    796

AAAACAGGTT TTCTTTTTTT AAAATGATAA CTTCAAACAA ATAGGTATTT CTTGATATAT    856

ATATGTATGT ATGTATGTGT GTGTGTGTGT GTGTGTGTAT GTGTGTGTTT GTGTATGTGT    916

ATATGTATGT ATGTATGTAT GTATGTATGT ATGTGTAGGA GAAAAGCAAA CTAAACAGTA    976

AATGAAAGAA AAAAATAAGT CAAATAAAAG TTTGATAATT                         1016
```

(2) INFORMATION FOR SEQ ID NO:4:

(i) SEQUENCE CHARACTERISTICS:
        (A) LENGTH: 208 amino acids
        (B) TYPE: amino acid
        (D) TOPOLOGY: linear (ii) MOLECULE TYPE: protein (xi) SEQUENCE DESCRIPTION: SEQ ID NO:4:

```
Phe Val Val Leu Leu Val Val Ala Ile Trp Ile Glu Met Ser Gln Gly
 1               5                  10                  15

Gln Gln Met Ile Lys Gln Cys Lys Cys Ser Asp Ile Ala Pro Cys Gln
                20                  25                  30

Leu Thr Ala Val Gln Ser Val Leu Pro Cys Ala Asp Gln Cys Gln Lys
            35                  40                  45

Tyr Ile Thr Ser Ile Gly Gly Asn Tyr Asp Gln Ile Ser Asn Cys Phe
        50                  55                  60

Lys Gln Lys Gln Ser Ile Ile Asn Asp Ala Met Lys Cys Ala Gln Asp
 65                 70                  75                  80

Ala Phe Pro Asn Ala Cys Ala Gln Gly Glu Pro Lys Met Val Pro Lys
                85                  90                  95

Arg Phe Gly Lys Gly Leu Gln Leu Ala Val Met Thr Asp Ile Asn Lys
            100                 105                 110

Glu Leu Gln Arg Met Gly Ile Ala Asn Gln Val Thr Gln Leu Ile Ser
        115                 120                 125

Gln Gly Arg Arg Phe Phe Lys Cys Phe Gln Ser Cys Met Met Lys Lys
    130                 135                 140

Leu Gly Ser Cys Ser Pro Asp Cys Gly Leu Asp Leu Pro Ser Asp Asn
145                 150                 155                 160

Val Met Val Gln Thr Val Lys Asn Cys Ala Gln Lys Ser Gly Ile Gln
                165                 170                 175

Thr Ala Ser Val Gln Asp Leu Cys Phe Cys Val Glu Gln Ala Gly Ile
            180                 185                 190

Arg Gln Leu Ser Asp Val Cys Pro Arg Ile Gln Ile Phe Lys Thr Lys
        195                 200                 205
```

(2) INFORMATION FOR SEQ ID NO:5:

(i) SEQUENCE CHARACTERISTICS:
        (A) LENGTH: 9 amino acids
        (B) TYPE: amino acid (C) STRANDEDNESS:
            (D) TOPOLOGY: linear (ii) MOLECULE TYPE: protein (xi) SEQUENCE DESCRIPTION: SEQ ID NO:5:

Asp Asp Cys Gly Asp Gly Ser Asp Glu
1               5

(2) INFORMATION FOR SEQ ID NO:6:

(i) SEQUENCE CHARACTERISTICS:
            (A) LENGTH: 16 amino acids
            (B) TYPE: amino acid
            (C) STRANDEDNESS:
            (D) TOPOLOGY: linear (ii) MOLECULE TYPE: protein (xi) SEQUENCE DESCRIPTION: SEQ ID NO:6:

Met Ala Gln Asp Ala Phe Pro Asn Ala Cys Ala Gln Gly Glu Pro Lys
1               5                   10                  15

(2) INFORMATION FOR SEQ ID NO:7:

(i) SEQUENCE CHARACTERISTICS:
            (A) LENGTH: 22 amino acids
            (B) TYPE: amino acid
            (C) STRANDEDNESS:
            (D) TOPOLOGY: linear (ii) MOLECULE TYPE: protein (xi) SEQUENCE DESCRIPTION: SEQ ID NO:7:

Ala Ile Ala Pro Cys Gln Leu Thr Ala Val Gln Ser Val Leu Pro Cys
1               5                   10                  15

Ala Asp Gln Cys Gln Lys
            20

(2) INFORMATION FOR SEQ ID NO:8:

(i) SEQUENCE CHARACTERISTICS:
            (A) LENGTH: 22 amino acids
            (B) TYPE: amino acid
            (C) STRANDEDNESS:
            (D) TOPOLOGY: linear (ii) MOLECULE TYPE: protein (xi) SEQUENCE DESCRIPTION: SEQ ID NO:8:

Leu Gly Ser Cys Ser Pro Asp Cys Gly Leu Asp Leu Pro Ser Asp Asn
1               5                   10                  15

Val Met Val Gln Asp Val
            20

(2) INFORMATION FOR SEQ ID NO:9:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 1..23
            (D) OTHER INFORMATION: /label= PRIMER (xi) SEQUENCE DESCRIPTION: SEQ ID NO:9:

CGGGATCCCG AGTTAAATAG TCG                                                               23

(2) INFORMATION FOR SEQ ID NO:10:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 1..17
            (D) OTHER INFORMATION: /label= PRIMER (xi) SEQUENCE DESCRIPTION: SEQ ID NO:10:

TGCAGGATCC TGCACCG                                                                      17

(2) INFORMATION FOR SEQ ID NO:11:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 1..50
            (D) OTHER INFORMATION: /label= PRIMER (xi) SEQUENCE DESCRIPTION: SEQ ID NO:11:

GAGAGAGAGA GAGAGAGAGA ACTAGTCTCG AGTTTTTTTT TTTTTTTTTT                                  50

(2) INFORMATION FOR SEQ ID NO:12:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 1..17
            (D) OTHER INFORMATION: /label= PRIMER (xi) SEQUENCE DESCRIPTION: SEQ ID NO:12:

TGYTCNCCNG AYTGYGG                                                                      17

(2) INFORMATION FOR SEQ ID NO:13:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 1..17

(D) OTHER INFORMATION: /label= PRIMER (xi) SEQUENCE DESCRIPTION: SEQ ID NO:13:

TGYAGTCCNG AYTGYGG                                                          17

(2) INFORMATION FOR SEQ ID NO:14:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 1..17
            (D) OTHER INFORMATION: /label= PROBE (xi) SEQUENCE DESCRIPTION: SEQ ID NO:14:

TGNACCATNA CRTTRTC                                                          17

(2) INFORMATION FOR SEQ ID NO:15:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 1..27
            (D) OTHER INFORMATION: /label= PROBE (xi) SEQUENCE DESCRIPTION: SEQ ID NO:15:

CTGTTTGAAC CATAACATTA CAGATGG                                               27

(2) INFORMATION FOR SEQ ID NO:16:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 1..25
            (D) OTHER INFORMATION: /label= PRIMER (xi) SEQUENCE DESCRIPTION: SEQ ID NO:16:

GTTGCAATAT GGGATCCAAT GAGCC                                                 25

(2) INFORMATION FOR SEQ ID NO:17:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_feature

-continued

```
    (B) LOCATION: 1..25
    (D) OTHER INFORMATION: /label= PRIMER (xi) SEQUENCE DESCRIPTION: SEQ ID NO:17:

CGCTAGTGCA GGATCCTCAA TACTC                                       25
```

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

What is claimed is:

1. An isolated nucleic acid molecule comprising a nucleic acid sequence selected from the group consisting of:
   (i) a nucleic acid sequence encoding a filariid p22U protein comprising the amino acid sequence of SEQ ID NO:4,
   (ii) a nucleic acid sequence encoding a fragment of SEQ ID NO:4 that elicits an IgG response;
   (iii) a nucleic acid sequence fully complementary to said nucleic acid sequence of (i); and,
   (iv) a nucleic acid sequence fully complementary to said nucleic acid sequence of (ii).

2. The isolated nucleic acid of claim 1, wherein said isolated nucleic acid molecule encodes a protein which selectively binds to immune serum derived from an animal that is immune to infection by *Dirofilaria immitis*, said immune serum being capable of inhibiting *Dirofilaria immitis* development.

3. The isolated nucleic acid molecule of claim 2 wherein said immune serum is derived from an animal immunized with a composition comprising *Dirofilaria immitis* larvae selected from the group consisting of third stage larvae, fourth stage larvae, and mixtures of third stage and fourth stage larvae.

4. The isolated nucleic acid molecule of claim 1, wherein said filariid is selected from the group consisting of Dirofilaria, Onchocerca, Brugia, Wuchereria, Loa, Acanthocheilonema, Dipetalonema, Setaria, Parafilaris, and Stephanofilaria filarial nematodes.

5. The isolated nucleic acid molecule of claim 1, wherein said filariid comprises a *Dirofilaria immitis* nematode.

6. The isolated nucleic acid molecule of claim 1, wherein said isolated nucleic acid molecule is derived from *Dirofilaria immitis*.

7. The isolated nucleic acid molecule of claim 1, wherein said nucleic acid sequence is selected from the group consisting of a nucleic acid sequence comprising SEQ ID NO:3 and a nucleic acid sequence fully complementary thereto.

8. The isolated nucleic acid molecule of claim 2, to wherein said isolated nucleic acid molecule is obtained by a method comprising:
   a) culturing a filariid expression library to promote production of proteins encoded by said library;
   b) contacting said library with said immune serum to permit binding of said immune serum to proteins expressed by said library that selectively bind to said immune serum;
   c) selecting a colony or phage plaque that contains a nucleic acid sequence encoding a protein that selectively binds to said immune serum; and,
   d) recovering said nucleic acid sequence encoding said protein from said colony or phage plaque.

9. A recombinant molecule comprising an isolated nucleic acid molecule set forth in claim 1 operatively linked to at least one transcription control sequence.

10. A recombinant cell comprising a cell transformed with an isolated nucleic acid molecule set forth in claim 1, wherein said recombinant cell expresses said isolated nucleic acid molecule.

11. A method to produce an isolated filariid p22U protein, comprising culturing a recombinant cell that expresses said protein, said protein being encoded by the isolated nucleic acid molecule of claim 1.

* * * * *